(12) United States Patent
Matsuzaki et al.

(10) Patent No.: US 8,938,620 B2
(45) Date of Patent: Jan. 20, 2015

(54) MEASUREMENT DEVICE AND METHOD OF CONTROLLING THE SAME

(75) Inventors: Natsume Matsuzaki, Osaka (JP); Yuichi Futa, Osaka (JP); Masao Nonaka, Osaka (JP)

(73) Assignee: Panasonic Corporation, Osaka (JP)

( * ) Notice: Subject to any disclaimer, the term of this patent is extended or adjusted under 35 U.S.C. 154(b) by 1084 days.

(21) Appl. No.: 12/995,801

(22) PCT Filed: Apr. 2, 2010

(86) PCT No.: PCT/JP2010/002425
§ 371 (c)(1),
(2), (4) Date: Dec. 2, 2010

(87) PCT Pub. No.: WO2010/113522
PCT Pub. Date: Oct. 7, 2010

(65) Prior Publication Data
US 2011/0093210 A1  Apr. 21, 2011

(30) Foreign Application Priority Data
Apr. 3, 2009  (JP) .................................. 2009-091608

(51) Int. Cl.
*G06F 19/00* (2011.01)
*A61B 5/021* (2006.01)
(Continued)

(52) U.S. Cl.
CPC ............... *A61B 5/021* (2013.01); *A61B 5/0002* (2013.01); *A61B 5/0006* (2013.01); *A61B 5/024* (2013.01);
(Continued)

(58) Field of Classification Search
CPC ..................... A61B 5/0002; H04L 9/3247

USPC .............................. 702/19; 713/180, 186, 189
See application file for complete search history.

(56) References Cited

U.S. PATENT DOCUMENTS

2004/0023295 A1* 2/2004 Hamilton et al. .............. 435/7.1
2004/0025030 A1* 2/2004 Corbett-Clark et al. ...... 713/186
(Continued)

FOREIGN PATENT DOCUMENTS

JP    2003-143135    5/2003
JP    2005-211172    8/2005
(Continued)

OTHER PUBLICATIONS

International Search Report issued Apr. 27, 2010 in corresponding International Application No. PCT/JP2010/002425.
(Continued)

*Primary Examiner* — Matthew Smithers
(74) *Attorney, Agent, or Firm* — Wenderoth, Lind & Ponack, L.L.P.

(57) ABSTRACT

A measurement device includes: a first measurement unit (101) measuring first biological data at least k times (k≥2) to obtain any k first measurement values; a distributed-signature generation unit (104) executing signature operations for the k first measurement values using any various k distributed-signature keys, respectively, to generate k distributed signatures, where the k distributed-signature keys can reconstruct a signature generation key only when all of them are available; a signature synthesis unit (106) synthesizing the k distributed signatures together to reconstruct a signature; and a steady state verification unit (107) verifying, using a signature verification key corresponding to the signature generation key, whether or not the signature reconstructed by the signature synthesis unit is correct, where the correctness of the signature means that the k first measurement values are same values.

12 Claims, 28 Drawing Sheets

(51) Int. Cl.
*A61B 5/00* (2006.01)
*A61B 5/024* (2006.01)
*H04L 9/08* (2006.01)
*H04L 9/30* (2006.01)
*H04L 9/32* (2006.01)

(52) U.S. Cl.
CPC ............ *G06F 19/3418* (2013.01); *H04L 9/085* (2013.01); *H04L 9/302* (2013.01); *H04L 9/3231* (2013.01); *H04L 9/3247* (2013.01); *A61B 2560/0271* (2013.01); *H04L 2209/805* (2013.01); *H04L 2209/88* (2013.01)
USPC ............................................ 713/189; 702/19

(56) References Cited

U.S. PATENT DOCUMENTS

| | | | | |
|---|---|---|---|---|
| 2004/0162472 | A1* | 8/2004 | Berson et al. | 600/323 |
| 2009/0312613 | A1* | 12/2009 | Henderson et al. | 600/301 |
| 2009/0318773 | A1* | 12/2009 | Jung et al. | 600/300 |
| 2012/0179380 | A1* | 7/2012 | Taylor et al. | 702/19 |
| 2014/0094707 | A1* | 4/2014 | Farringdon et al. | 600/509 |

FOREIGN PATENT DOCUMENTS

| | | |
|---|---|---|
| JP | 2005-245833 | 9/2005 |
| JP | 2006-127161 | 5/2006 |
| JP | 2007-229116 | 9/2007 |
| WO | 2009/119079 | 10/2009 |

OTHER PUBLICATIONS

Bruce Schneier, "Applied Cryptography", $2^{nd}$ Edition, revised $2^{nd}$ version, published by Wiley, 1996, pp. 528-529.

Tatsuaki Okamoto et al., "Gendai Ango (Modern Cryptography)", published by Sangyo Tosho Kabushiki-kaisha, 1997, pp. 214-215 (with partial English translation).

D. E. Knuth, "The art of computer programming (4)", $2^{nd}$ version, SAIENSU SHA Co., Ltd., 1981, pp. 334-335 (with partial English translation).

* cited by examiner

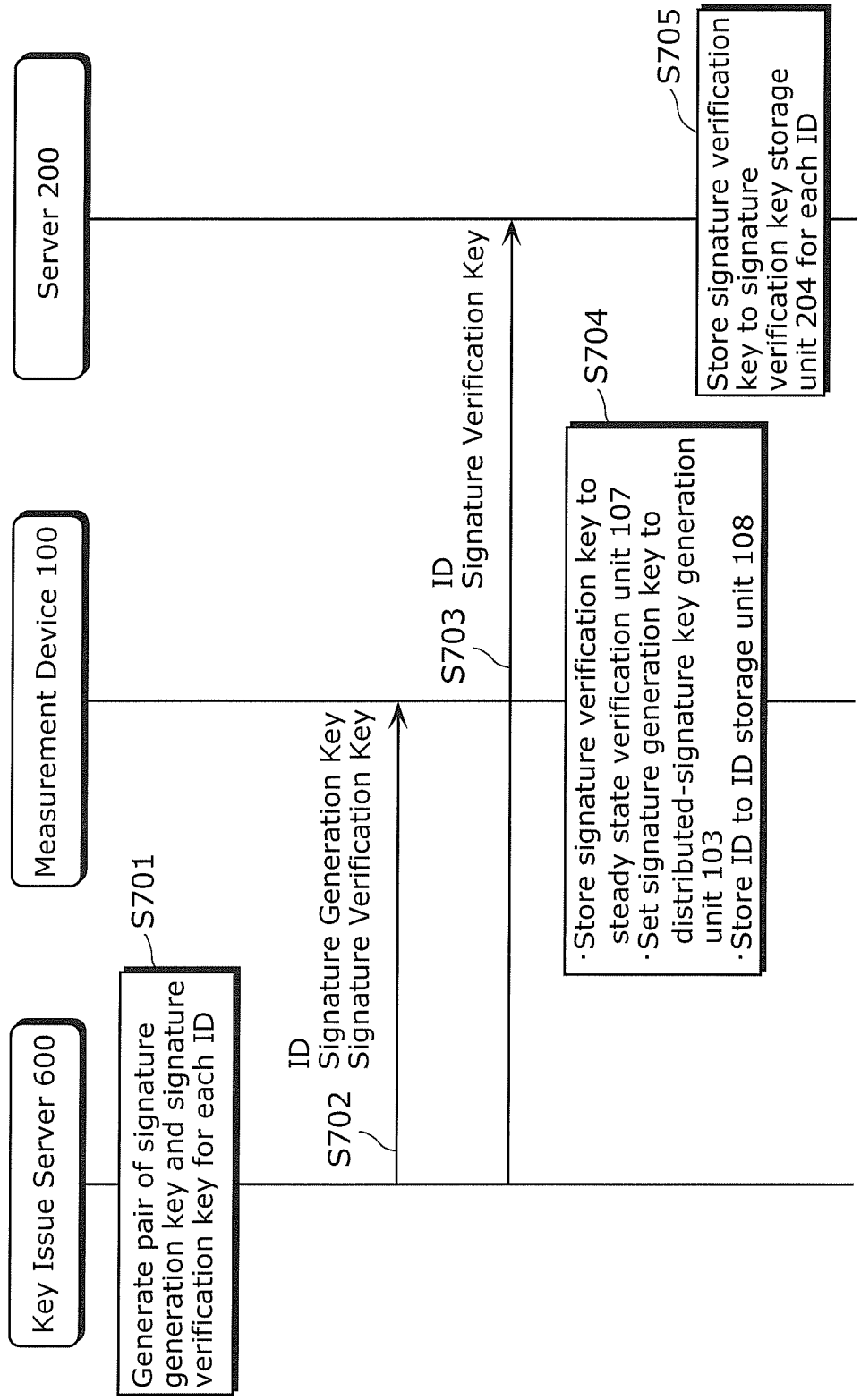

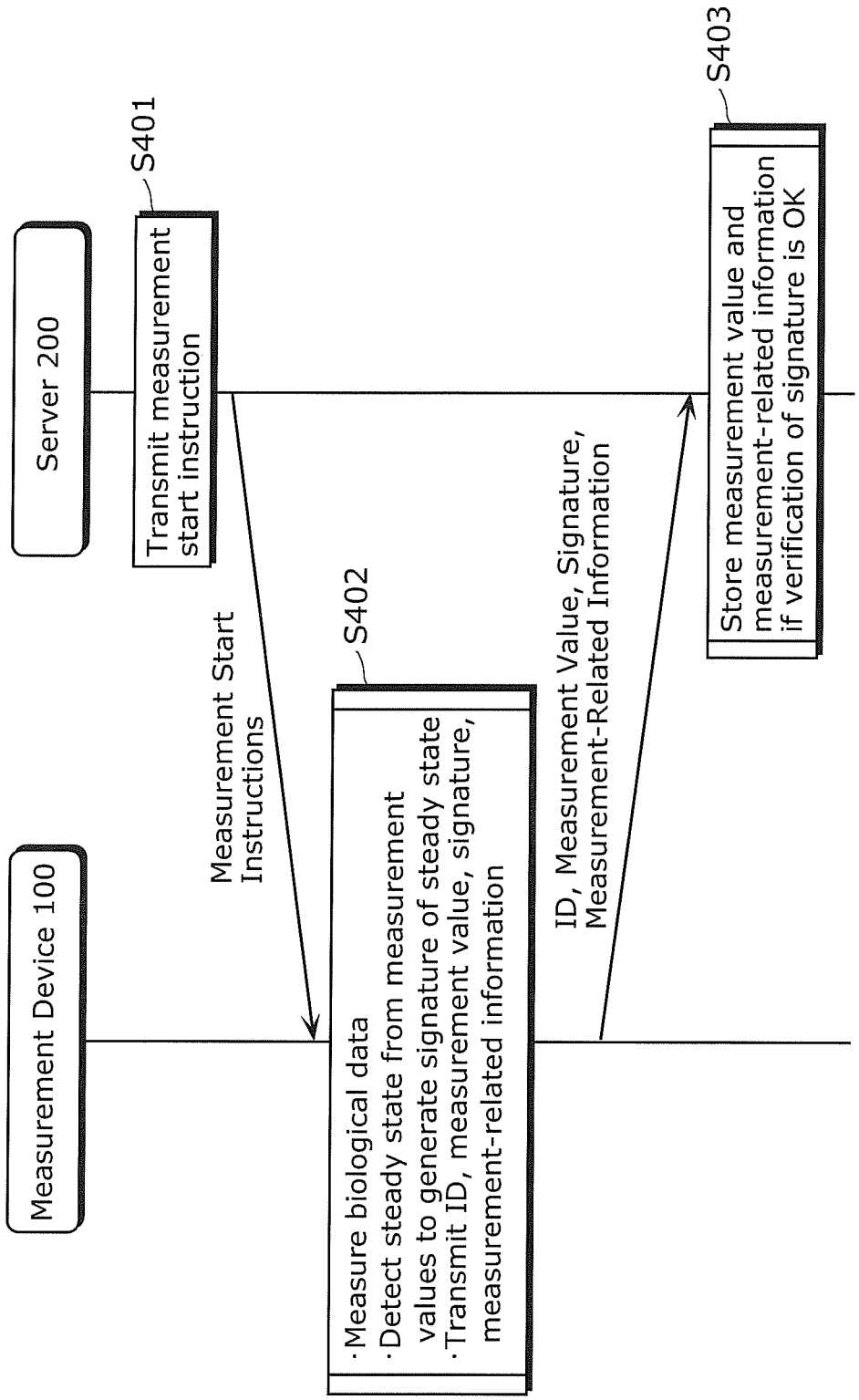

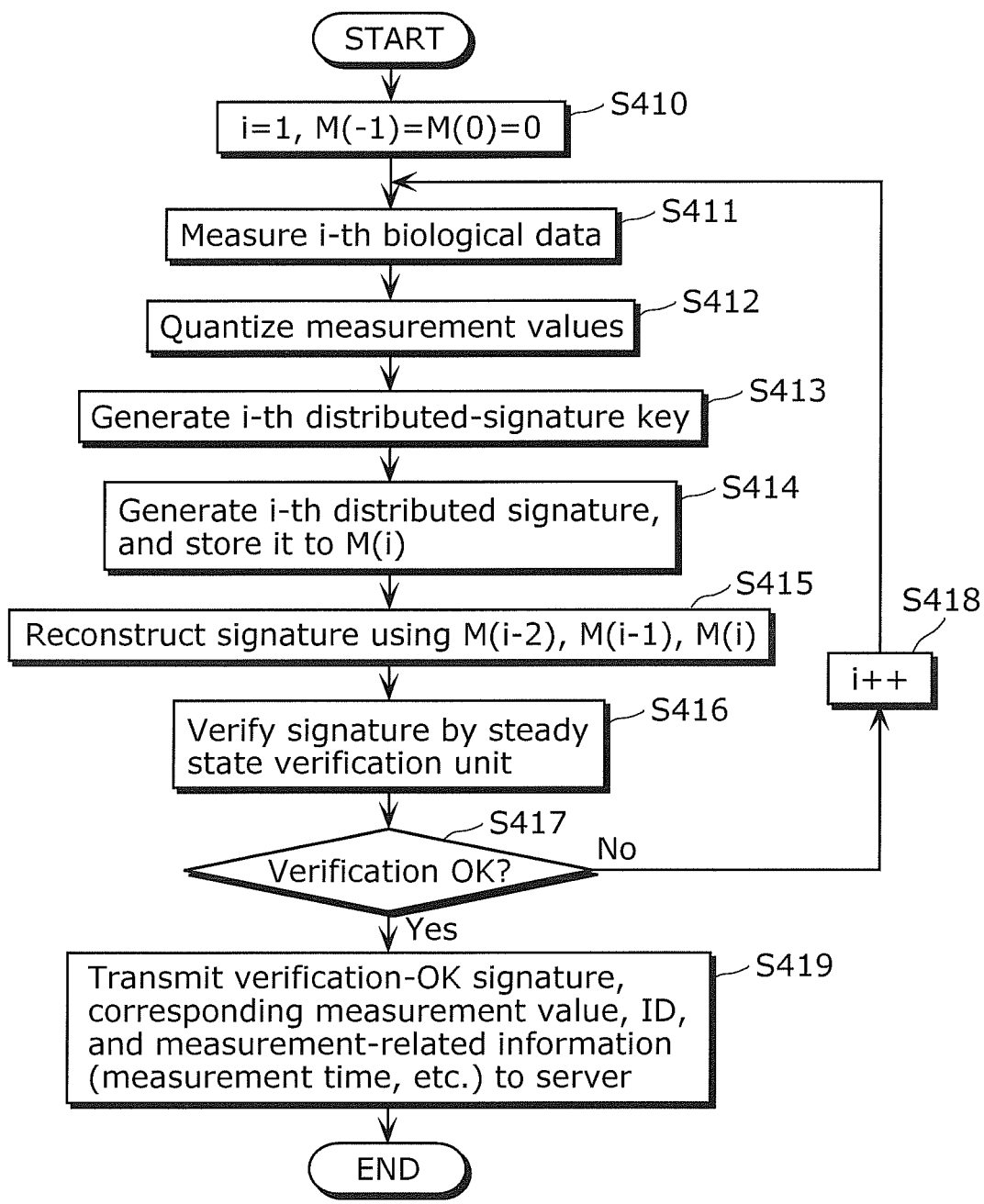

In case where threshold value is 3

FIG. 11

| Address of Server 200 | Measurement Value | Signature | ID | Measurement Date/Time | Measurement Place | ......... |

Measurement-Related Information: Measurement Date/Time, Measurement Place, ...

FIG. 26

| ID | Measurement Date/Time | Second Measurement Value: Electrocardiogram File (File Name) |
|---|---|---|
| 12345 | 2008/12/1 9:00 | ¥12345¥081201¥0900 |
| 12345 | 2008/12/1 12:05 | ¥12345¥081201¥1205 |

207

MEASUREMENT DEVICE AND METHOD OF CONTROLLING THE SAME

TECHNICAL FIELD

The present invention relates to a measurement device and a method controlling the same to measure biological data including pulse, blood pressure, blood sugar level, or the like.

BACKGROUND ART

In recent years, measurement devices are examined to measure biological data such as pulse, blood pressure, and blood sugar level and transmit the result of the measurement to servers in hospitals, insurance companies, and the like. Such a measurement device is connected to a server via a communication network. The measurement device, which allows a subject to always wear the device, automatically measures biological data of subject's health such as blood pressure at a desired time and transmit the result of the measurement to the server as needed.

Thereby, when any unusual health situation happens on the subject, a specialized institution such as a medical institution can deal with the situation speedily and appropriately (see Patent Reference 1, for example).

PRIOR ART

Patent Reference

[Patent Reference 1] Japanese Unexamined Patent Application Publication No. 2005-211172

DISCLOSURE OF INVENTION

Problems that Invention is to Solve

The above-described conventional technology, however, has the following problem.

The biological data should be measured when the subject is in rest state, so that a physician in a hospital or the like can diagnose more correctly based on the measurement result. For example, when a physician or the like directly measures a blood pressure of a patient by himself/herself, the physician can perform the measurement while confirming that the patient is at rest. However, if measured biographic data is merely transmitted to a server as disclosed in the above conventional technology, a physician in a hospital cannot check whether or not the received biological data is measured when the patient is at rest. As a result, the physician cannot diagnose correctly based on the measurement result.

In order to address the above problem, an object of the present invention is to provide a measurement device and a method of controlling the same which can determine whether biological data is measured in rest state of a user.

Means to Solve the Problems

In accordance with an aspect of the present invention for achieving the object, there is provided a measurement device including: a first measurement unit configured to measure first biological data at least k times, where k≥2, to obtain any k first measurement values; a distributed-signature generation unit configured to execute signature operations for the k first measurement values using any various k distributed-signature keys, respectively, to generate k distributed signatures, the k distributed-signature keys being capable of reconstructing a signature generation key only when all of the k distributed-signature keys are available; a signature synthesis unit configured to synthesize the k distributed signatures together to reconstruct a signature; and a steady state verification unit configured to verify, using a signature verification key corresponding to the signature generation key, whether or not the signature reconstructed by the signature synthesis unit is correct, where the correctness of the signature means that the k first measurement values are same values.

With the above structure, a secret sharing scheme originally employed in cryptographic technologies is used to determine whether or not the first biological data is measured while a user is in rest state. Thereby, without a sensor or the like for detecting rest state of the user, it is possible to determine whether or not the first biological data is measured in user's rest state, by determining whether or not the signature reconstructed from the k distributed signatures is correct. As a result, the measurement device needs only a simple structure to determine whether or not the first biological data is measured in user's rest state.

It should be noted that the present invention can be implemented not only as the above measurement device including the above characteristic processing units, but also as: a method of controlling the measurement device which includes steps performed by the characteristic processing units included in the measurement device: a program causing a computer to execute the characteristic steps of the controlling method; and the like. Of course, such a program can be distributed by a computer-readable nonvolatile recording medium such as a Compact Disc-Read Only Memory (CD-ROM) or by a communication network such as the Internet.

Effects of the Invention

The present invention can provide a measurement device and a method of controlling the same which can determine whether biological data is measured in rest state of a user.

BRIEF DESCRIPTION OF DRAWINGS

FIG. 7 is a sequence diagram illustrating processing performed by the measurement device, the server, and a key issue server in initialization in the biological data management system employing the measurement device and the method of controlling the measurement device according to the first embodiment of the present invention.

FIG. 8 is a sequence diagram illustrating processing performed by the measurement device and the server in biological data measurement in the biological data management system employing the measurement device and the method of FIG. 9 is a flowchart of step S402 in FIG. 8.

FIG. 11 is a diagram illustrating a format example of data transmitted by the measurement device according to the first embodiment of the present invention.

FIG. 26 is a diagram of a memory structure of a measurement value storage unit illustrated in FIG. 24.

BEST MODE FOR CARRYING OUT THE INVENTION

Figure 1:
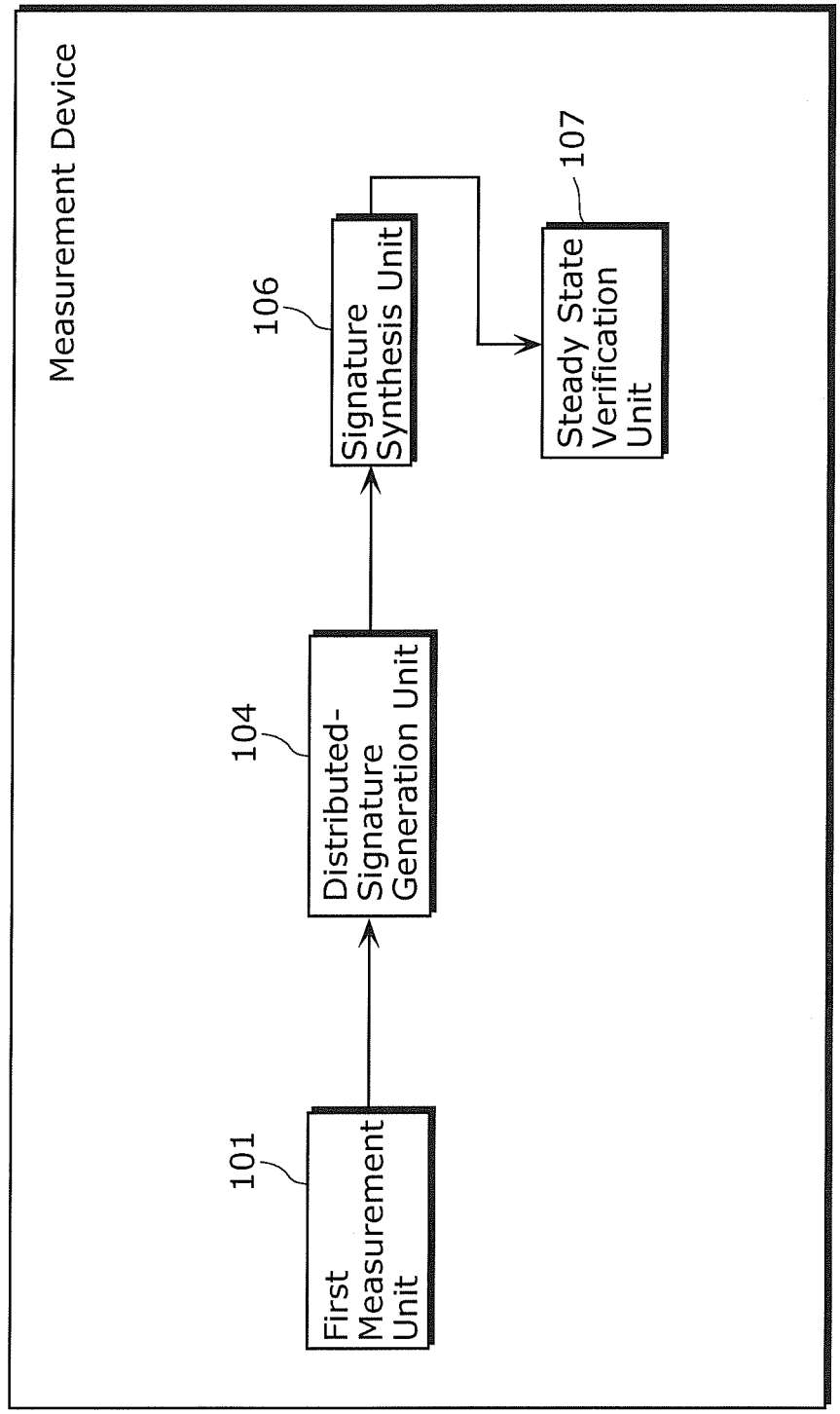
FIG. 1 is a block diagram illustrating an internal structure of a measurement device according to an aspect of the present invention.

FIG. 1 is a block diagram illustrating an internal structure of a measurement device according to an aspect of the present invention.

According to the aspect of the present invention, a measurement device including: a first measurement unit configured to measure first biological data at least k times, where k≥2, to obtain any k first measurement values; a distributed-signature generation unit configured to execute signature operations for the k first measurement values using any various k distributed-signature keys, respectively, to generate k distributed signatures, the k distributed-signature keys being capable of reconstructing a signature generation key only when all of the k distributed-signature keys are available; a signature synthesis unit configured to synthesize the k distributed signatures together to reconstruct a signature; and a steady state verification unit configured to verify, using a signature verification key corresponding to the signature generation key, whether or not the signature reconstructed by the signature synthesis unit is correct, where the correctness of the signature means that the k first measurement values are same values.

According to the aspect of the present invention, a secret sharing scheme originally employed in cryptographic technologies is used to determine whether or not the first biological data is measured while a user is in rest state. Thereby, without a sensor for detecting rest state of the user, the measurement device can determine whether or not the first biological data is measured in the user's rest state, by determining whether or not the signature reconstructed from the k distributed signatures is correct. As a result, the measurement device needs only a simple structure to determine whether or not the first biological data is measured in user's rest state.

In addition, the determination that the reconstructed signature is not correct means that the first measurement values are different depending on respective measurement times. Therefore, such determination is considered to indicate that the first biological data is measured in user's rest state. As a result, the measurement device can use the simple method to eliminate first measurement values calculated when the user is in unrest state.

Moreover, the first measurement values themselves can be used as operational elements in the signature operations. Thereby, the first measurement values have two functions, serving originally as measurement values of the first biological data, and also as the operational elements in the signature operations. As a result, the measurement device can use only a simple structure to determine whether or not the first biological data is measured in user's rest state.

It is preferable that a result of a multiplication of the signature generation key and the signature verification key is a predetermined value, each of the signature operations is exponentiation where a corresponding one of the k distributed-signature keys or the signature generation key is an exponent, the signature generation key is generated by summing values of respective multiplications of the k distributed-signature keys by respective predetermined coefficients, the distributed-signature generation unit is configured to generate the k distributed signatures by executing the exponentiation for the k first measurement values, respectively, a base of the exponentiation being each of the k first measurement values, and an exponent of the exponentiation being a distributed-signature key corresponding to the each of the k first measurement values among the k distributed-signature keys, the signature synthesis unit is configured to calculate the signature by raising the k distributed signatures respectively to power of the respective predetermined coefficients to generate k exponentiation results, and multiplying the k exponentiation results together, and the steady state verification unit is configured to determine by the verification that the signature reconstructed by the signature synthesis unit is correct, when a predetermined verification equation is satisfied, a left-hand side of the predetermined verification equation being exponentiation where the signature is a base and the signature verification key is an exponent, and a right-hand side of the predetermined verification equation being a target first measurement value from among the k first measurement values.

According to the aspect of the present invention, if the reconstructed signature satisfies the predetermined verification equation, it is determined that the reconstructed signature is correct. In short, in the aspect of the present invention, each of the signature operations is exponentiation. In addition, the signature generation key and the distributed signatures have the relationship described above. Therefore, when the k first measurement values are the same values, a product (a result of a multiplication) of the k distributed signatures is equal to a result of signing the first measurement values by the signature generation key. Furthermore, according to the relationship in which a product of the signature generation key and the signature verification key is 1, a result of verifying the signature using the signature verification key is equal to each of the first measurement values. Therefore, using the k first measurement values, it is possible to determine whether or not the k first measurement values are same values, namely, whether or not the first biological data is measured in user's rest state.

It is also possible in the above measurement device that the measurement device further includes a quantization unit configured to quantize the k first measurement values obtained by the first measurement unit, wherein the distributed-signature generation unit is configured to generate the k distributed signatures by executing the signature operations for the k first measurement values using the k distributed-signature keys, respectively, the k first measurement values being quantized by the quantization unit.

According to the aspect of the present invention, the quantization unit can absorb a difference among pieces of the first biological data calculated by the first measurement unit. As a result, it is possible to prevent such a minor difference from causing false determination that the fist biological data is not measured in user's rest state.

It is further possible in the above measurement device that the measurement device further includes a transmission unit configured to transmit, to an external server, one of the k first measurement values together with the signature reconstructed by the signature synthesis unit, when the steady state verification unit determines by the verification that the signature is correct.

According to the aspect of the present invention, the first measurement value can be transmitted together with the reconstructed signature to the external server.

It is still further possible in the above measurement device that the measurement device further includes a second measurement unit configured to measure second biological data to obtain a second measurement value, the second biological data being different from the first biological data measured by the first measurement unit and being measured in parallel to the measurement of the first biological data, wherein the steady state verification unit is further configured to permit the second measurement value obtained by the second measurement unit to be transmitted outside, when the steady state verification unit determines by the verification that the signature reconstructed by the signature synthesis unit is correct.

According to the aspect of the present invention, the first biological data measured as the operational elements in the signature operations is different from the second biological data measured as an actual objective. In this case, even if a piece of the second biological data, which is an actual objective to be measured, consists of plural pieces of data, such as blood pressure data consisting of an upper value (maximum blood pressure) and a lower value (minimum blood pressure), a piece of a different kind of biological data, such as pulse, which has a single measurement value, is used as the first biological data. As a result, it is possible to determine, by using the first biological data, whether or not the second biological data is measured in user's rest state. Therefore, the measurement device needs only a simple structure to determine whether or not the second biological data is measured in user's rest state.

In addition, even if the second biological data, which is an actual objective to be measured, is not useful to determine whether or not the second biological data is measured in user's rest state, such as electrocardiogram data not having steady values, it is possible to determine, by using the first measurement values, whether or not the second biological data is measured in user's rest state.

It is still further possible in the above measurement device that the measurement device further includes a first reference value storage unit configured to store, as a reference value, a criterion value to be used as a criterion for the k first measurement values, wherein the distributed-signature generation unit is configured to generate the k distributed signatures by executing the signature operations for the reference value and (k−1) first measurement values among the k first measurement values using the k distributed-signature keys, respectively.

According to the aspect of the present invention, the k distributed signatures are generated from (a) the reference value that is a criterion value used as a criterion of the first measurement values and (b) (k−1) first measurement values. By reconstructing a signature from the k distributed signatures including the distributed signature of the reference value, the determination is made that the reconstructed signature is not correct, when each of the (k−1) distributed signatures, which are calculated by measuring the first biological data (k−1) times, is not the same as the distributed signature of the reference value. Therefore, if the first biological data measures as the operational elements in the signature operations is different from the second biological data measured as an actual objective, it is possible to determine whether or not the second biological data is measured in user's rest state and also whether or not the user of the second biological data is the same as the user of the first biological data.

It is still further possible in the above measurement device that the measurement device further includes: a second signature generation unit configured to generate a signature of the second measurement value using, as a signature generation key, the signature reconstructed by the signature synthesis unit; and a transmission unit configured to transmit the second measurement value together with the signature of the second measurement value to an external server, when the steady state verification unit permits the second measurement value to be transmitted outside.

According to the aspect of the present invention, the signature of the second measurement value is generated using, as the signature generation key, the signature reconstructed by the signature synthesis unit. Thereby, the external server, which receives the signature of the second measurement value and the second measurement value, can determine whether or not the second measurement value is a measurement value of the second biological data of the user who is the same as the user of the first biological data.

It is still further possible in the above measurement device that the measurement device further includes: a second encryption unit configured to encrypt the second measurement value using, as an encryption key, the signature reconstructed by the signature synthesis unit; and a transmission unit configured to transmit the second measurement value encrypted by the second encryption unit to an external server, when the steady state verification unit permits the second measurement value to be transmitted outside.

According to the aspect of the present invention, the second measurement value is encrypted using, as an encryption key, the signature reconstructed by the signature synthesis unit. Thereby, the measurement device needs only a simple structure to protect privacy of the user by assuring to keep confidential the second measurement value transmitted to the external server.

It is still further possible that the first biological data is pulse data, and the second measurement value is electrocardiogram data.

According to the aspect of the present invention, the first biological data may be pulse data and the second biological data may be electrocardiogram data.

It is still further possible that the first measurement unit is configured to measure the first biological data temporally consecutive k times to obtain the k first measurement values.

According to the aspect of the present invention, the signature synthesis unit can reconstruct the signature by gathering distributed signatures corresponding to a consecutive predetermined number of times. Thereby, the measurement device can determine whether or not the first biological data is measured in the situation where the user is kept in rest state.

In accordance with another aspect of the present invention, there is provided a method of controlling a measurement device, the method including: measuring first biological data at least k times, where k≥2, to obtain any k first measurement values; executing signature operations for the k first measurement values using any various k distributed-signature keys, respectively, to generate k distributed signatures, the k distributed-signature keys being capable of reconstructing a signature generation key only when all of the k distributed-signature keys are available; synthesizing the k distributed signatures together to reconstruct a signature; and verifying, using a signature verification key corresponding to the signature generation key, whether or not the signature reconstructed is correct, where the correctness of the signature means that the k first measurement values are same values.

In accordance with still another aspect of the present invention, there is provided a program causing a computer to execute: measuring first biological data at least k times, where k≥2, to obtain any k first measurement values; executing signature operations for the k first measurement values using any various k distributed-signature keys, respectively, to generate k distributed signatures, the k distributed-signature keys being capable of reconstructing a signature generation key only when all of the k distributed-signature keys are available; synthesizing the k distributed signatures together to reconstruct a signature; and verifying, using a signature verification key corresponding to the signature generation key, whether or not the signature reconstructed is correct, where the correctness of the signature means that the k first measurement values are same values.

In accordance with still another aspect of the present invention, there is provided an integrated circuit including: a first measurement unit configured to measure first biological data at least k times, where k≥2, to calculate any k first measurement values; a distributed-signature generation unit configured to execute signature operations for the k first measurement values using any various k distributed-signature keys, respectively, to generate k distributed signatures, the k distributed-signature keys being capable of reconstructing a signature generation key only when all of the k distributed-signature keys are available; a signature synthesis unit configured to synthesize the k distributed signatures together to reconstruct a signature; and a steady state verification unit configured to verify, using a signature verification key corresponding to the signature generation key, whether or not the signature reconstructed by the signature synthesis unit is correct, where the correctness of the signature means that the k first measurement values are same values.

First Embodiment

Figure 2:
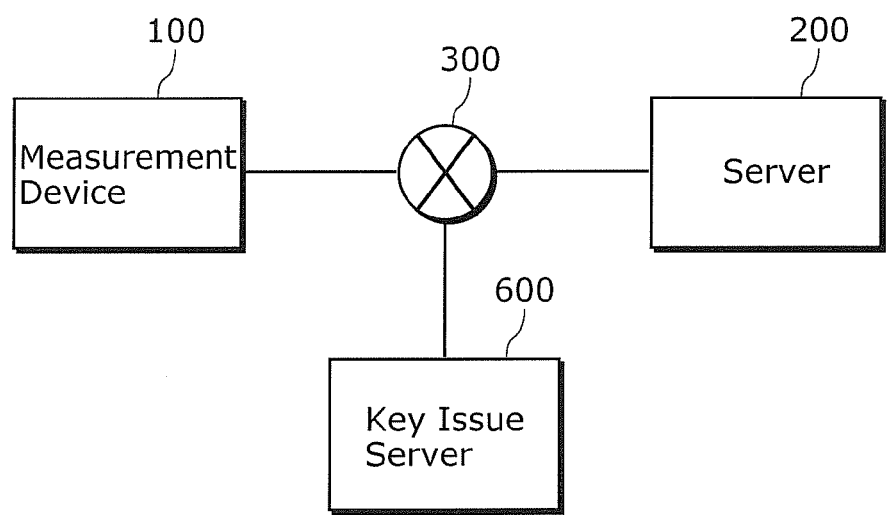
FIG. 2 is a diagram illustrating configuration of a biological data management system employing a measurement device and a method of controlling the measurement device according to a first embodiment of the present invention.

The following describes a measurement device and a method of controlling the measurement device according to one of the aspects of the present invention with reference to the drawings. FIG. 2 is a diagram illustrating configuration of a biological data management system employing a measurement device and a method of controlling the measurement device according to a first embodiment of the present invention. Referring to FIG. 2, the biological data management system according to the first embodiment includes a measurement device 100, a server 200, and a key issue server 600 which are connected to one another via a network 300. Here, the server 200 is placed in a medical institution such as a hospital, an insurance company, or the like. The key issue server 600 is placed in a key issue center that issues signature generation keys and signature verification keys. It is assumed here that the key issue server 600 exchanges data with the measurement device 100 or the server 200 via the network 300 such as the Internet. However, they may perform the data exchange via the network 300 such as a Local Area Network (LAN) or via a recording medium such as a Universal Serial Bus (USB) memory.

The measurement device 100 has: a function of measuring biological data such as pulse, blood pressure, or blood sugar level of a user; a function of determining whether or not the user is in rest state; and a function of generating a signature indicating that the biological data is measured in rest state of the user. The measurement device 100 also has a function of communicating with the server 200 to transmit a result of the measurement and the signature to the server 200. In addition, the measurement device 100 receives a signature generation key and a signature verification key from the key issue server 600.

The server 200 has a function of gathering the measurement result and the signature from the measurement device 100 to determine whether or not the signature is correct. The server 200 also manages the gathered measurement result for each user in a database.

The network 300 is implemented as the Internet, a local network such as an intra network in a hospital, or the like. The network 300 may be a wired or wireless network.

Figure 3:
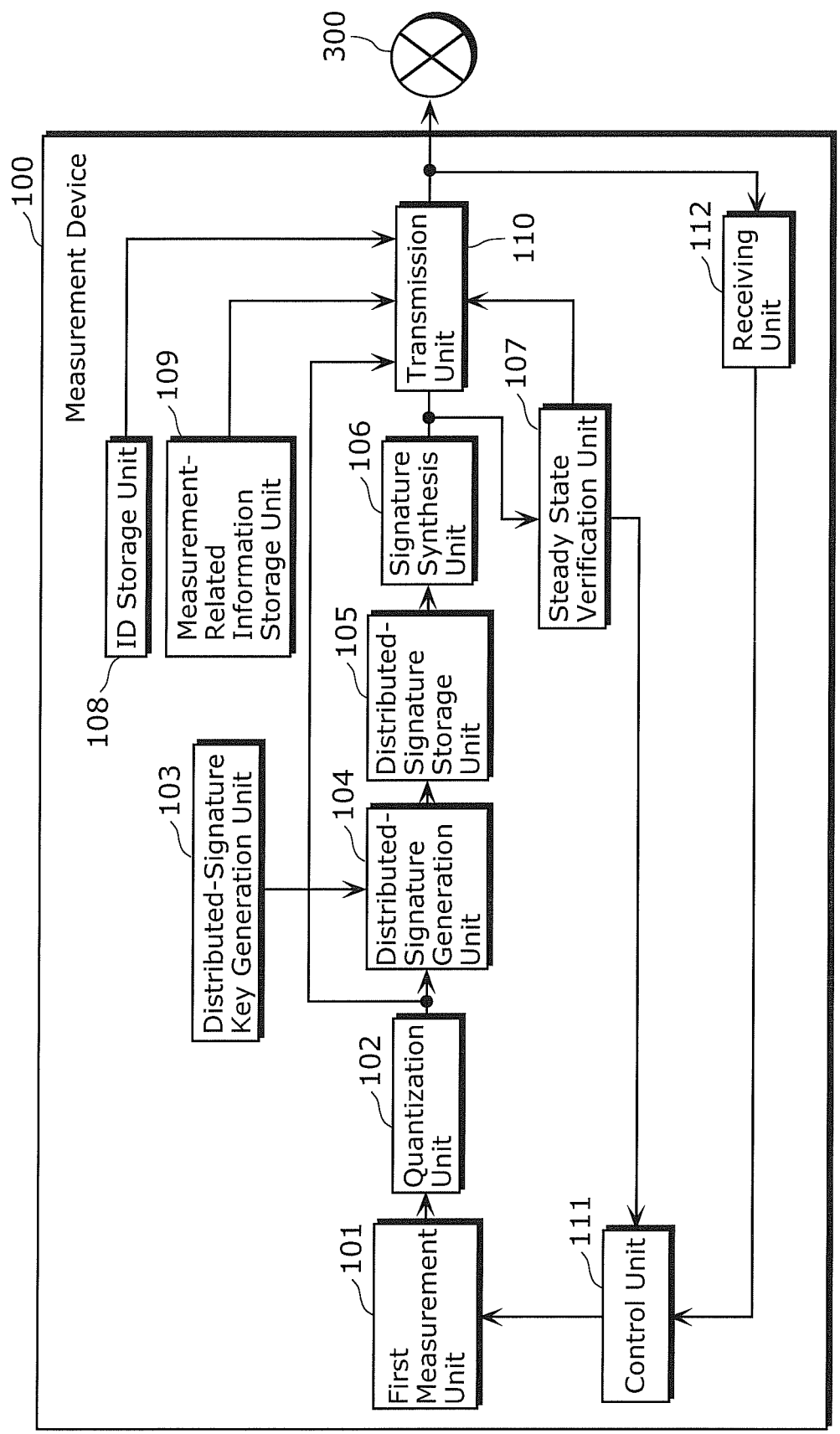
FIG. 3 is a block diagram illustrating an internal structure of the measurement device according to the first embodiment of the present invention.

FIG. 3 is a block diagram illustrating an internal structure of the measurement device 100 according to the first embodiment of the present invention. The measurement device 100 detects whether or not the user is in rest state in measuring biological data, and generates a signature indicating that the biological data is measured while the user is in rest state. In order to detect rest state, the measurement device 100 measures biological data a plurality of times to generate one measurement result. When measurement values of biological data measured a predetermined number of times from among all measurement values biological data measured a plurality of times have steady values, namely, the same values, then the measurement device 100 determines that the user is in rest state and thereby generates a signature indicating that the measurement values are measured in rest state.

The measurement device 100 performs (a) the determination of equality among measurement values measured a predetermined number of times and (b) the generation of a signature regarding the measurement values at the same time using a secret sharing scheme. The secret sharing scheme is a technique of dividing a certain secret data into n pieces, so that the original data can be reconstructed only when different k pieces among the n pieces are obtained. Here, k and n, each of which is an integer of 2 or more, satisfy a relationship of k≤n (see Non-Patent Reference 1 and Non-Patent Reference 2, for example).

[Non-Patent Reference 1] "APPLIED CRYPTOGRAPHY", Bruce Schneier, revised 2nd version, (US), published by WILEY, 1996, pp. 528-529

[Non-Patent Reference 2] "Gendai Ango (Modern Cryptography)", Tatsuaki Okamoto, Hirosuke Yamamoto, published by Sangyo Tosho Kabushiki-kaisha, 1997, pp. 214-215

Here, in the first embodiment, the predetermined number is k. The measurement device 100 performs signing (hereinafter, referred to as "distributed signatures") for each of k measurement values corresponding to the predetermined number of times, using distributed-signature keys into which a predetermined signature generation key is divided by the secret sharing scheme. The measurement device 100 synthesizes the k distributed signatures to reconstruct a signature, and verifies the synthesized signature using a signature verification key corresponding to the above signature generation key. If the synthesized signature is generated correctly, it is understood that the k measurement values have the same values. It should be noted that the first embodiment is given in the case of k=3, but k may have any other value.

The following describes each of the functional blocks included in the measurement device 100.

The measurement device 100 includes a first measurement unit 101, a quantization unit 102, a distributed-signature key generation unit 103, a distributed-signature generation unit 104, a distributed-signature storage unit 105, a signature synthesis unit 106, a steady state verification unit 107, an ID storage unit 108, a measurement-related information storage unit 109, a transmission unit 110, a control unit 111, and a receiving unit 112.

In receiving instructions for starting measurement from the control unit 111, the first measurement unit 101 measures biological data that is to be measured.

The quantization unit 102 quantized each measurement value generated by the first measurement unit 101. Thereby, if a difference or a variation occurs in a predetermined range among the measurement values, the difference and variation can be absorbed.

The distributed-signature key generation unit 103 distributes a signature generation key into pieces at respective measurement timings "i" (where i=1, 2, . . . ) to generate distributed-signature keys "d(i)". The signature generation key is previously set in the measurement device 100 in initialization. Here, the distributed-signature keys "d(i)" vary depending on the measurement timings "i". It is assumed in the first embodiment that the distributed-signature key generation unit 103 generates the distributed-signature keys "d(i)" sequentially for the respective measurement timings "i". It is also possible that the distributed-signature key generation unit 103 previously generates the distributed-signature keys "d(i)" before measuring pieces of biological data and sequentially outputs them at respective measurement timings "i". The summary of the initialization will be described later with reference to FIG. 7.

The distributed-signature generation unit 104 signs, at each measurement timing "i", a measurement value "m(i)" of biological data provided from the quantization unit 102, using the respective distributed-signature key "d(i)" provided from the distributed-signature key generation unit 103, thereby generating a distributed-signature "M(i)". For example, when "i=1", the distributed-signature generation unit 104 signs a measurement value "m(1)" by a distributed-signature key "d(1)" to generate a distributed signature "M(1)". In this manner, the distributed-signature generation unit 104 generates a distributed-signature "M(i)" for each measurement timing "i", sequentially generating a distributed-signature "M(2)" when "i=2", a distributed-signature "M(3)" when "i=3", and so on.

The distributed-signature storage unit 105 holds the distributed-signature "M(i)" generated at each measurement timing "i". Here, at least three distributed signatures are stored in the distributed-signature storage unit 105. Therefore, the distributed-signature storage unit 105 may be implemented as a shift register.

The signature synthesis unit 106 synthesizes a predetermined number "k" of distributed signatures among n distributed signatures from a distributed signature "M(1)" to a distributed signature "M(n)" to reconstruct a signature. In the first embodiment, the predetermined number "k" of distributed signatures are synthesized together, by setting, as a criterion, the distributed signatures "M(i)" generated at each measurement timing "i". More specifically, the signature synthesis unit 106 synthesizes a predetermined number "k" of distributed signatures "M(i), M(i−1), . . . , M(i−(k−1))" up to the target distributed signature "M(i)" as the criterion. For instance, it is assumed that a value of the predetermined number "k" is "k=3", namely, three distributed signatures are to be synthesized. Under the assumption, when the distributed signature "M(n)" is generated at a measurement timing "i=n", the signature synthesis unit 106 synthesizes three distributed signatures "M(n)", "M(n−1)", and "M(n−2)" to reconstruct a signature, by setting the distributed signature "M(n)" as a criterion.

The steady state verification unit 107 verifies, using a predetermined signature verification key, whether or not the reconstructed signature is correct. More specifically, if the reconstructed signature satisfies a predetermined verification equation described later, the steady state verification unit 107 determines that the reconstructed signature is correct so as to determine that the measurement values measured the predetermined number of times "k" are steady values. For example, in the situation where a value of the predetermined number "k" is "k=3", the steady state verification unit 107 verifies whether or not the predetermined verification equation is satisfied by a signature reconstructed by synthesizing three distributed signatures "M(n)", "M(n−1)", and "M(n−2)". Then, if the reconstructed signature satisfies the verification equation, the steady state verification unit 107 determines that the signature is correct, and thereby determines that three measurement values "m(n)", "m(n−1)", and "m(n−2)" have the same values, namely, "m(n)=m(n−1)=m(n−2)". Here, the predetermined signature verification key is previously set in the steady state verification unit 107 in initialization.

The ID storage unit 108 holds identification (ID) for identifying the measurement device 100.

The measurement-related information storage unit 109 holds information related to measurement (hereinafter, referred to as "measurement-related information"). The measurement-related information is, for example, date and time of measurement (measurement date/time), a position information of the measuring measurement device 100 which is detected by a global positioning system (GPS), or the like.

The transmission unit 110 generates data in a predetermined format including an eventual measurement value, a reconstructed signature, the ID, and the measurement-related information which are obtained when the steady state verification unit 107 determines that the predetermined number of measurement values have the same values. Then, the transmission unit 110 transmits the generated data to the server 200.

The control unit 111 controls each processing performed by the measurement device 100. For example, when the receiving unit 112 receives a measurement start instruction from the server 200, the control unit 111 controls the measurement device 100 to start measuring biological data. Furthermore, when the steady state verification unit 107 does not detect a steady state from the measurement result, the control unit 111 controls the measurement device 100 to perform the measurement once more.

Figure 4:
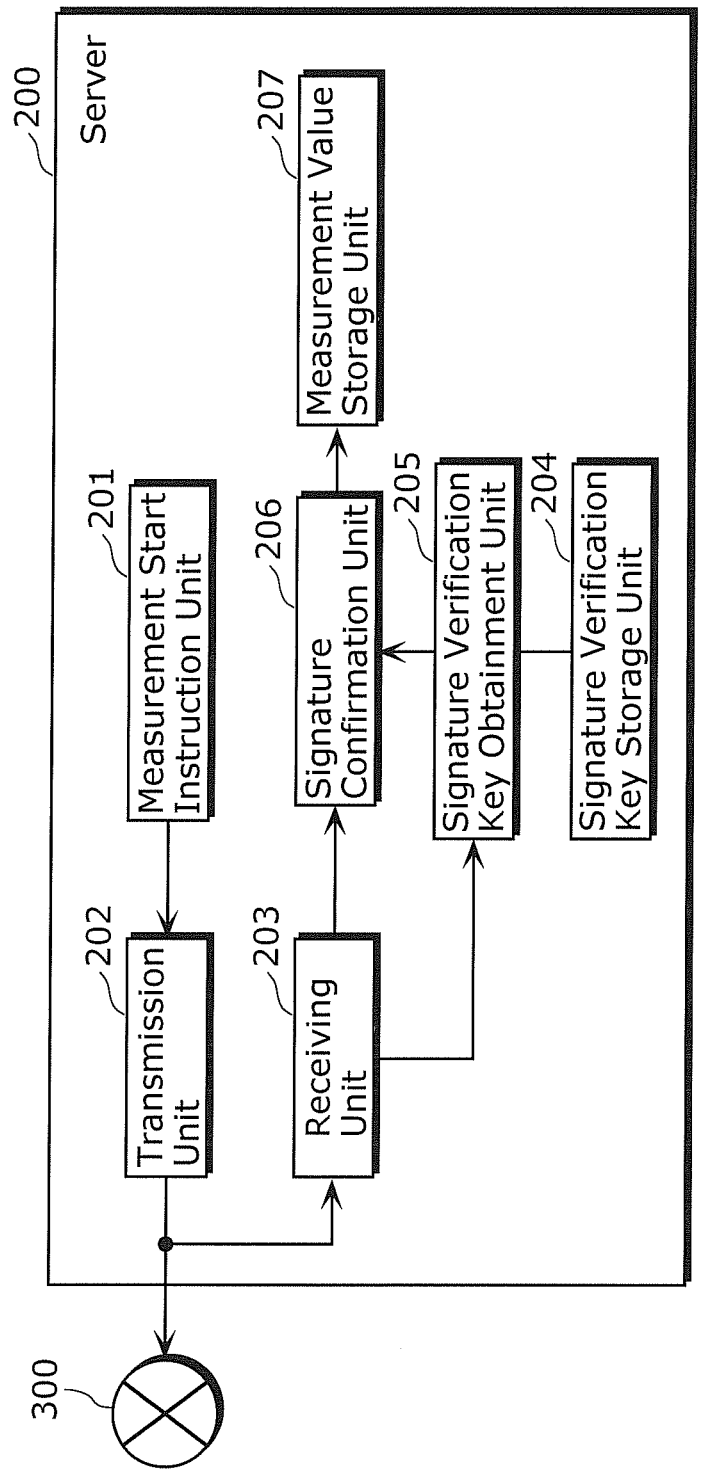
FIG. 4 is a block diagram illustrating an internal structure of a server according to the first embodiment of the present invention.

FIG. 4 is a block diagram illustrating an internal structure of the server 200 according to the first embodiment of the present invention.

The server 200 includes a measurement start instruction unit 201, a transmission unit 202, a receiving unit 203, a signature verification key storage unit 204, a signature verification key obtainment unit 205, a signature confirmation unit 206, and a measurement value storage unit 207.

The measurement start instruction unit 201 instructs the measurement device 100 to start measuring biological data. A timing of issuing the measurement start instruction is set by a physician in a medical institution, for example. The timing may be a predetermined timing of "once in 30 minutes" or "once in an hour", or may be a random timing.

The transmission unit 202 transmits the measurement start instruction to the measurement device 100.

The receiving unit 203 receives, from the measurement device 100, data in a predetermined format which includes a measurement value, a signature, ID, and measurement-related information.

The signature verification key storage unit 204 stores a signature verification key in association with the ID of the measurement device 100, to be used to verify the signature gathered from the measurement device 100. The signature verification key is previously set in the signature verification key storage unit 204 in initialization. The signature verification key storage unit 204 will be described in more detail later with reference to FIG. 5.

The signature verification key obtainment unit 205 obtains, from the signature verification key storage unit 204, a signature verification key associated with the ID gathered from the measurement device 100, and provides the signature verification key to the signature confirmation unit 206.

The signature confirmation unit 206 verifies the signature gathered from the measurement device 100, by using the signature verification key obtained from the signature verification key storage unit 204. In more detail, the signature confirmation unit 206 determines that the signature is correct, if the signature satisfies a predetermined verification equation.

The measurement value storage unit 207 stores the measurement value and the measurement-related information in association with the ID. Here, if the signature verified by the signature confirmation unit 206 is correct, these pieces of information are written by the signature confirmation unit 206 to the measurement value storage unit 207. The measurement value storage unit 207 will be described in more detail later with reference to FIG. 6.

Figure 5:
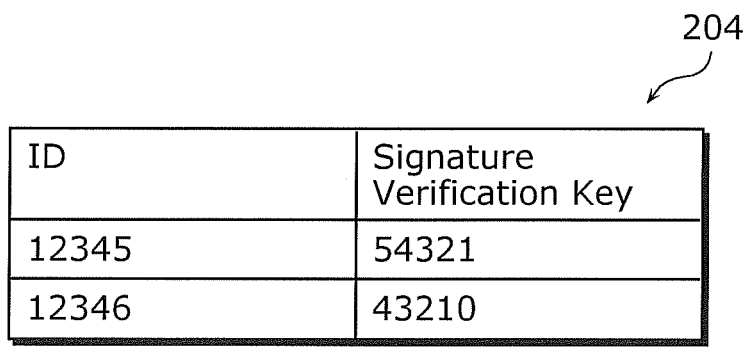
FIG. 5 is a diagram of a memory structure of a signature verification key storage unit illustrated in FIG. 4.

FIG. 5 is a diagram of a memory structure of the signature verification key storage unit 204 illustrated in FIG. 4. Referring to FIG. 5, the signature verification key storage unit 204 has an item "ID" and an item "signature verification key". The signature verification key storage unit 204 manages the ID of the measurement device and the signature verification key in association with each other. In the item "ID", the ID for identifying the measurement device 100 is stored. In the item "signature verification key", the signature verification key for verifying any signature transmitted from the measurement device 100 is stored.

For instance, in the case of FIG. 5, the signature verification key storage unit 204 holds signature verification keys for a measurement device 100 having ID "12345" and another measurement device 100 having ID "12346". The measurement device 100 having ID "12345" is associated with the signature verification key "54321" while the measurement device 100 having ID "12346" is associated with the signature verification key "43210".

Figure 6:
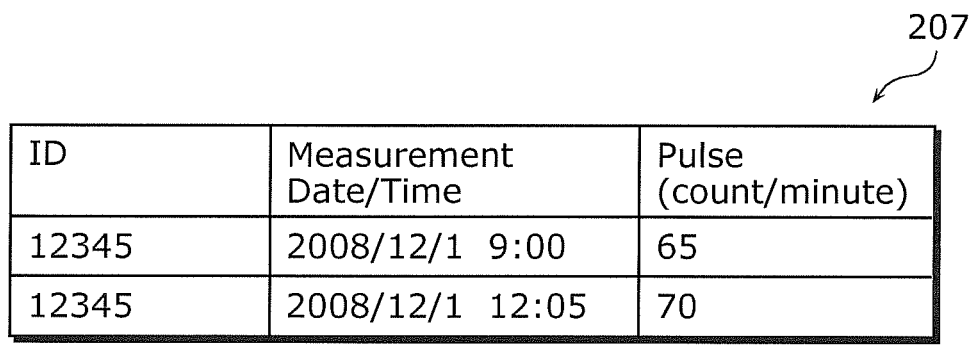
FIG. 6 is a diagram of a memory structure of a measurement value storage unit illustrated in FIG. 4.

FIG. 6 is a diagram of a memory structure of the measurement value storage unit 207 illustrated in FIG. 4. The following describes the situation where biological data to be measured is data of pulse. Referring to FIG. 6, the measurement value storage unit 207 has an item "ID", an item "measurement date/time", and an item "pulse (count/minute)". The measurement value storage unit 207 manages ID of the measurement device 100, measurement date/time, and a measurement value of pulse in association with one another. In the item "ID", the ID for identifying the measurement device 100 is stored. In the item "measurement date/time", date and time of measuring pulse are recorded. In item "pulse (count/minute)", a measurement value of pulse is recorded.

For example, in the case of FIG. 6, the measurement value storage unit 207 records a measurement date/time and an eventual measurement value of pulse for each of two measurement processes performed by the measurement device having ID "12345". More specifically, it is indicated that the measurement device 100 having ID "12345" measures pulse at "9:00 AM, Dec. 1, 2008" and that a measurement value of the measurement is "65". Likewise, it is also indicated that the measurement device 100 having ID "12345" measures pulse at "12:05 PM, Dec. 1, 2008" and that a measurement value of the measurement is "70".

The following describes the measurement device 100 having the above structure and steps of the method of controlling the measurement device 100 with reference to the figures.

FIG. 7 is a sequence diagram illustrating processing performed by the measurement device 100, the server 200, and the key issue server 600 in initialization, in the biological data management system employing the measurement device 100 and the method of controlling the measurement device 100 according to the first embodiment of the present invention. In the initialization, the measurement device 100 is to be set with ID, a signature generation key, and a signature verification key, and the server 200 is to be set with the ID of the measurement device 100 and the signature verification key.

First of all, the key issue server 600 generates a pair of a signature generation key and a signature verification key in association with ID of the measurement device 100 (S701). Then, the key issue server 600 distributes the ID, the signature generation key, and the signature verification key to the measurement device 100 (S702), and the ID and the signature verification key to the server 200 (S703).

Here, in the case of using a Rivest Shamir Adleman (RSA) signature, for example, the signature generation key and the signature verification key are generated by:

(1) generating large prime numbers p and q;
(2) calculating n=p×q; and
(3) calculating arbitrary e and d which satisfy e×d=1 mod λ (where λ=LCM (p−1, q−1)).

Here, "e" represents a signature verification key, and "d" represents a signature generation key. In the above manner, the key issue server 600 generates a pair of a signature verification key "e" and a signature generation key "d" in association with ID.

In receiving the ID, the signature generation key "d", and the signature verification key "e" from the key issue server 600, the measurement device 100 sets the ID to the ID storage unit 108, the signature generation key "d" to the distributed-signature key generation unit 103, and the signature verification key "e" to the steady state verification unit 107 (S704). It should be noted that the setting of the signature generation key "d" and the signature verification key "e" to the measurement device 100 may be performed in a factory before shipping the measurement device 100 to a market or in a shop after the shipping.

In receiving the ID and the signature verification key from the key issue server 600, the server 200 sets the ID and the signature verification key in association with each other in the signature verification key storage unit 204 (S705). For example, in the situation where the ID has a value "12345" and the signature verification key "e" has a value "54321", the ID value "12345" is set in the item "ID" and the signature verification key value "54321" is set in the item "signature verification key" in the signature verification key storage unit 204 illustrated in FIG. 5.

FIG. 8 is a sequence diagram illustrating processing performed by the measurement device 100 and the server 200 in biological data measurement, in the biological data management system employing the measurement device 100 and the method of controlling the measurement device 100 according to the first embodiment of the present invention.

First, the server 200 transmits instruction for starting measurement to the measurement device 100 via the network 300 (S401).

According to the measurement start instruction, the measurement device 100 measures biological data to be measured. Here, the measurement device 100 performs the measurement a predetermined number of times to eventually obtain one measurement value. Then, based on measurement values measured the predetermined number of times, the measurement device 100 detects that a user is in rest state during the measurement. The measurement device 100 thereby generates a signature indicating the measurement is performed while the user is in rest state. In addition, when it is detected that the user is in rest state, the measurement device 100 generates data in a predetermined format which includes the (final) measurement value, the signature, the ID of the measurement device 100, and measurement-related information regarding the above measurement, and transmits the generated data to the server 200 (S402). The step S402 will be described in more detail later with reference to FIG. 9.

In receiving the data in the predetermined format which includes the measurement value, the signature, the ID, and the measurement-related information, the server 200 verifies using the signature verification key whether or not the signature is correct. If the signature is correct, then the server 200 stores the measurement value and the measurement-related information to the measurement value storage unit 207 (S403). The step S403 will be described in more detail later with reference to FIG. 13.

FIG. 9 is a flowchart of step S402 in FIG. 8. In the step, the measurement device 100 measures pieces of biological data a plurality of times, and detects, based on k measurement values corresponding to a predetermined number of times among the plurality of times, that a user is in rest state during the measurement, and generates a signature indicating that the measurement is performed in user's rest state. The measurement device 100 transmits a measurement value measured in the rest state and the signature to the server 200. The following describes the step in the situation where the predetermined number of times k is "k=3". In the following description, i represents each measurement timing. In addition, each quantized measurement value is represented by m(i) and each distributed-signature key is represented by d(i). The predetermined number of times may be consecutive numbers, or inconsecutive numbers.

Previously, the control unit 111 sets the variable i to be "1" as initialization, so that "i=1". Here, when a distributed signature "M(1)" is generated for a first measurement process, the measurement device 100 cannot synthesize three distributed signatures "M(1)", "M(0)", and "M(−1)" together, by setting the distributed signature "M(1)" as a criterion, because the distributed signatures "M(−1)" and "M(0)" have no value. Therefore, the control unit 111 substitutes an initial value "0" to each of the distributed signatures "M(−1)" and "M(0)" in this initialization, so that "M(−1)=0" and "M(0)=0" (S410). After this initialization, the measurement device 100 performs the previously-described detection of rest state and the previously-described generation of a signature indicating the rest state.

First, the first measurement unit 101 performs the first measurement of biological data (S411). Then, the quantization unit 102 quantized a measurement value of the first measurement (S412). The quantization can absorb a difference or variation that would occur in a predetermined range among measurement values.

Next, the distributed-signature key generation unit 103 generates an i-th distributed-signature key d(i) (S413).

Figure 10A:
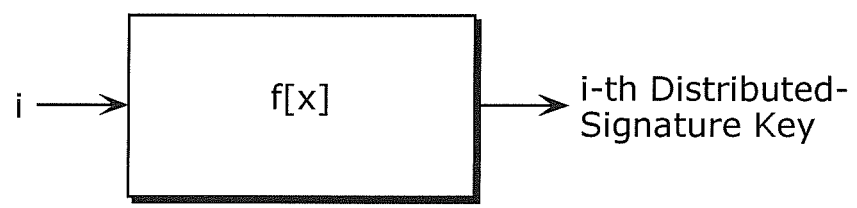
FIG. 10A is a diagram for explaining a principle of a method of generating a distributed-signature key.
Figure 10B:
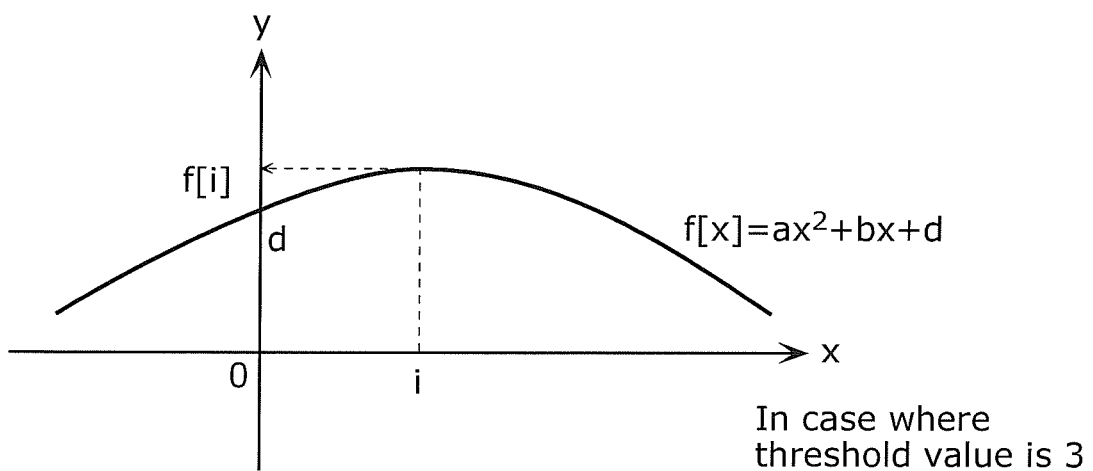
FIG. 10B is a graph plotting details of a function f(x) illustrated in FIG. 10A.

Here, a method of generating a distributed-signature key d(i) is described with reference to FIGS. 10A and 10B. FIGS. 10A and 10B explain the method of generating a distributed-signature key d(i) using the secret sharing scheme described with reference to FIG. 3.

FIG. 10A is a diagram for explaining a principle of the method of generating a distributed-signature key d(i). On the other hand, FIG. 10B is a graph plotting details of a function f(x) illustrated in FIG. 10A. FIG. 10B illustrates an example of the method of generating a distributed-signature key d(i) in the case of k=3. As illustrated in FIG. 10A, the distributed-signature key generation unit 103 enters a value of each measurement timing i to an arbitrary function f(x) to generate a distributed-signature key d(i).

More specifically, in the case of "k=3", as illustrated in FIG. 10B, the distributed-signature key generation unit 103 calculates an arbitrary second-order polynomial "f(x)=ax$^2$+bx+d" (where a and b are arbitrary constants) when a constant term (an intercept of FIG. 10B) is a signature generation key d. After that, the operation is performed by further executing the mod λ operation. The signature generation key d is transmitted from the key issue server at S702 in initialization described with reference to FIG. 7. Here, the i-th distributed signature key d(i) has a value of f(i) in the situation where i is set to x in the second-order polynomial, namely, a y-coordinate value in the situation where i is set in an x-coordinate in the coordinate graph of FIG. 10B. For example, in the case of "i=1", a distributed-signature key d(1) is calculated as "d(1)=f(1)=a+b+d", while in the case of "i=2", a distributed-signature key d(2) is calculated as "d(2)=f(2)=4a+2b+d".

As described above, the distributed-signature key generation unit 103 previously sets an arbitrary second-order polynomial f(x) to calculate a value of a second-order polynomial f(i) for each measurement timing i to generate a distributed-signature key d(i).

Since the second-order polynomial is previously determined when arbitrary three points are certain on the polynomial, a signature generation key d that is an intercept of the polynomial is reconstructed. Here, the reconstruction of the signature generation key d can employ Lagrange interpolating method. The Lagrange interpolating method is a technique of calculating a polynomial passing a predetermined number of points (see Non-Patent Reference 3, for example).

[Non-Patent Reference 3] "The art of computer programming (4)", D. E. KNUTH, translated by Keisuke Nakagawa, 2nd revision, SAIENSU SHA Co., Ltd. 1981, pp. 334-335

The employment of Lagrange interpolating method can reconstruct the second-order polynomial f(x) using the following equation (1), when the three points are (x1, y1), (x2, y2), and (x3, y3).

$$f(x) = [\{(x-x2) \times (x-x3)\}/\{(x1-x2) \times (x1-x3)\}] \times y1 + [\{(x-x1) \times (x-x3)\}/\{(x2-x1) \times (x2-x3)\}] \times y2 + [\{(x-x1) \times (x-x2)\}/\{(x3-x1) \times (x3-x2)\}] \times y3 \quad \text{Equation (1)}$$

Since the signature generation key d is an intercept, the signature generation key d has a value obtained by substituting x in the above second-order polynomial "f(x)" so that "d=f(0)". It should be noted that it has been described that the distributed-signature key is expressed on the y-coordinate of f(i) corresponding to the i-th measurement, but may be a point (pair of x-coordinate and y-coordinate) on the polynomial.

The above-described method of generating a distributed-signature key d(i) allows the measurement device 100 to distribute distributed-signature keys d chronologically. In the first embodiment, the measurement device 100 uses the method to determine whether or the three measurement values "m(i)", "m(i−1)", and "m(i−2)" are steady values.

Referring back to FIG. 9, after step S413, the distributed-signature generation unit 104 generates a distributed signature "M(i)" using a measurement value m(i) and a distributed-signature key d(i) and stores the distributed signature "M(i)" in the distributed-signature storage unit 105 (S414). Here, the above-described secret sharing scheme can express a distributed signature "M(i)" as "M(i)=m(i)$^{d(i)}$ mod n" using a measurement value m(i) and a distributed-signature key d(i).

Next, the signature synthesis unit 106 synthesizes the three distributed signatures "M(i)", "M(i−1)", and "M(i−2)" together, by setting the distributed signature "M(i)" as a criterion, so as to generate a signature S(i) (S415). The synthesis method is based on the following equation (2).

$$S(i) = \{M(i-2)^{Li(i-2)} \times M(i-1)^{Li(i-1)} \times M(i)^{Li(i)}\} \bmod n \quad \text{Equation (2)}$$

It should be noted that the exponents Li(i−2), Li(i−1), and Li(i) in the above equation correspond to respective coefficients in an equation for calculating an intercept of second-order polynomial passing three points (i−2, d(i−2)), (i−1, d(i−1)), (i, d(i)) using the Lagrange interpolating method. More specifically, the exponents are expressed by the following equation (3).

$$Li(i-2) = \frac{\{(0-(i-1)) \times (0-i)\}}{\{((i-2)-(i-1)) \times ((i-2)-i)\}}$$
$$= [\{i \times (i-1)\}/2] \bmod \lambda$$

$$Li(i-1) = \frac{\{(0-(i-2)) \times (0-i)\}}{\{((i-1)-(i-2)) \times ((i-1)-i)\}}$$
$$= -[\{i \times (i-2)\}] \bmod \lambda$$

$$Li(i) = \{(0-(i-2)) \times (0-(i-1))\}/\{(i-(i-2)) \times (i-1)\}$$
$$= [\{(i-1) \times (i-2)\}/2] \bmod \lambda \quad \text{Equation (3)}$$

Use of the equation (3) satisfies the following equation (4).

$$d(i-2) \times Li(i-2) + d(i-1) \times Li(i-1) + d(i) \times Li(i) = d \bmod \lambda \quad \text{Equation (4)}$$

Next, the steady state verification unit 107 verifies a signature S(i) using a signature verification key e set at S702 in FIG. 7 (S416), thereby determining whether or not the signature S(i) satisfies a predetermined verification equation (S417). More specifically, the steady state verification unit 107 confirms whether or not the following verification equation (equation (5)) is satisfied using the signature verification key e.

$$S(i)^e = m(i) \bmod n \quad \text{Equation (5)}$$

Then, if the above verification equation (equation (5)) is satisfied, the steady state verification unit 107 determines that the three measurement values "m(i)", "m(i−1)", and "m(i−2)" are steady values, namely "m(i)=m(i−1)=m(i−2)". The above verification equation can determine whether or not the three measurement values have the same values, for the following reason.

If the three measurement values have steady values, namely, "m(i−2)=m(i−1)=m(i)", the following equation (6) is satisfied from the equation (4).

$$S(i) = M(i-2)^{Li(i-2)} \times M(i-1)^{Li(i-1)} \times M(i)^{Li(i)} \bmod n \quad \text{Equation (6)}$$
$$= (m(i)^{d(i-2)})^{Li(i-2)} \times (m(i)^{d(i-1)})^{Li(i-1)} \times (m(i)^{d(i)})^{Li(i)} \bmod n$$
$$= m(i)^{d(i-2) \times Li(i-2) + d(i-1) \times Li(i-1) + d(i) \times Li(i)} \bmod n$$
$$= m(i)^d \bmod n$$

If exponentiation where S(i) in equation (6) is a base and the signature verification key e is an exponent is executed, the following equation (7) that is the verification equation (5) is satisfied according to the relational equation e×d=1 mod λ described with reference to FIG. 7.

$$S(i)^e = m(i)^{e \times d} \bmod n = m(i) \bmod n \quad \text{Equation (7)}$$

On the other hand, if the three measurement values are not steady values, the above verification equation (equation (5)) is not satisfied.

It should be noted that it has been described that the relational equation $e \times d = 1 \mod \lambda$ is used according to a structure of the RSA cryptography, but the relational equation may be $e \times d = c \mod \lambda$ where c is a predetermined constant. In this case, regarding the verification equation of the equation (7), it is confirmed whether or not to satisfy $S(i)^e = m(i)^c \mod n$.

There is another method of generating a distributed-signature key d(i), in addition to the above method using a polynomial.

First, a signature generation key d of the RSA signature is divided into arbitrary three distributed-signature keys "d1", "d2", and "d3" satisfying the following equation.

$$d = (d1 + d2 + d3) \mod \lambda$$

Then, the three distributed-signature keys are used repeatedly in order as an i-th distributed-signature key d(i). For example, three distributed-signature keys "d1", "d2", and "d3" are used repeatedly in order as a distributed-signature key d(i), such as "d(1)=d1, d(2)=d2, d(3)=d3", "d(4)=d1, d(5)=d2, d(6)=d3", "d(7)=d1, d(8)=d2, d(9)=d3", . . . .

In this case, when the distributed-signature generation unit 104 calculates a distributed signature "$M(i) = m(i)^{d(i)} \mod n$". The signature synthesis unit 106 multiplies a distributed signature "$M(i-1) = m(i-1)^{d(i-1)} \mod n$" by a distributed signature "$M(i-2) = m(i-2)^{d(i-2)} \mod n$" to generate a signature S(i).

$$S(i) = M(i) \times M(i-1) \times M(i-2) \mod n \quad \text{Equation (8)}$$

Then, using the signature verification key e set at S702 of FIG. 7, the steady state verification unit 107 confirms whether or not the equation (5) is satisfied.

$$S(i)^e = m(i) \mod n \quad \text{Equation (5)}$$

If the above verification equation (equation (5)) is satisfied, the steady state verification unit 107 determines that the three measurement values "m(i)", "m(i−1)", and "m(i−2)" are steady values, namely "m(i)=m(i−1)=m(i−2)". The above verification equation (equation (5)) can determine whether or not the three measurement values have the same values, for the following reason.

If the three measurement values have steady values, namely, "m(i−2)=m(i−1)=m(i)", the following equation (9) is satisfied from the equation (8).

$$\begin{aligned} S(i) &= M(i-2) \times M(i-1) \times M(i) \quad \text{Equation (9)} \\ &= m(i)^{d(i-2)} \times m(i)^{d(i-1)} \times m(i)^{d(i)} \mod n \\ &= m(i)^{d(i-2)+d(i-1)+d(i)} \mod n \\ &= m(i)^d \mod n \end{aligned}$$

If exponentiation where S(i) in equation (9) is a base and the signature verification key e is an exponent is executed, the following equation (10) that is the verification equation (5) can be satisfied according to the relational equation $e \times d = 1 \mod \lambda$ described with reference to FIG. 7.

$$S(i)^e = m(i)^{e \times d} \mod n = m(i) \mod n$$

On the other hand, if the three measurement values are not steady values, the above verification equation (equation (5)) is not satisfied.

Referring back to FIG. 9, as described above, at S417, if it is determined that the signature S(i) satisfies the above verification equation (equation (5)), then it means that the three measurement values "m(i)", "m(i−1)", and "m(i−2)" are the same values. In this case (Yes at S417), the steady state verification unit 107 provides the measurement value m(i) and the signature S(i) to the transmission unit 110. Then, the transmission unit 110 generates data in a predetermined format as illustrated in FIG. 11 which includes not only the measurement value m(i) and the signature S(i) but also ID of the measurement device 100 and measurement-related information, and transmits the data to the server 200 (S419).

On the other hand, at S417, if it is determined that the signature S(i) does not satisfy the above verification equation (equation (5)), then it means that the three measurement values "m(i)", "m(i−1)", and "m(i−2)" are not the same values. In this situation (No at S417), the control unit 111 adds 1 to the variable i (S418). The first measurement unit 101 thereby measure biological data again (S418→S411). Then, until the signature S(i) satisfies the above verification equation (equation (5)), in other words, until three measurement values "m(i)", "m(i−1)", and "m(i−2)" have the same values, the measurement device 100 repeats the processing S411 to S418.

Figure 12:
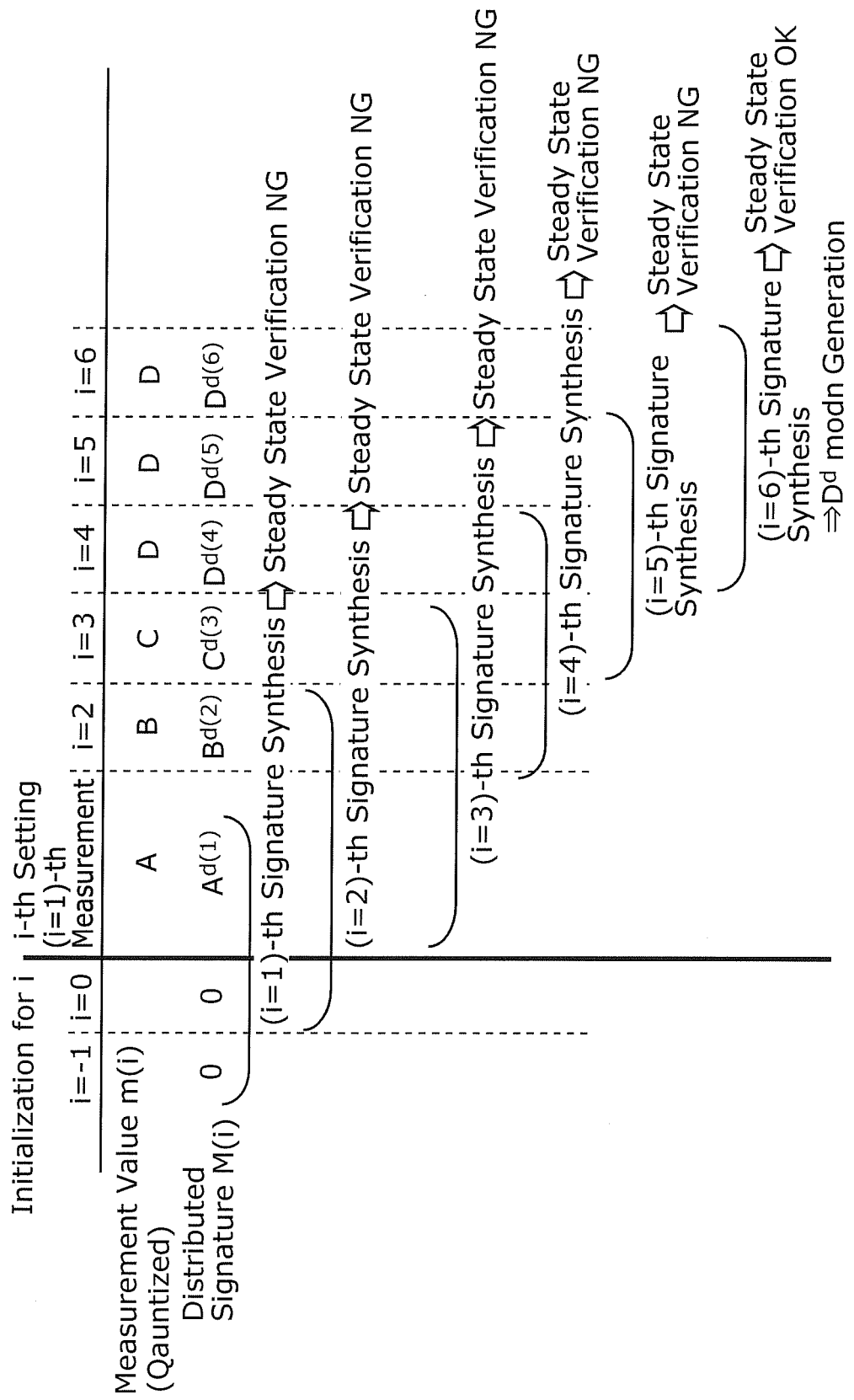
FIG. 12 is a conceptual diagram illustrating a signature synthesis method and a signature verification method used in the measurement device according to the first embodiment of the present invention.

The following describes the method of verifying the steady state from S415 to S418 in more detail with reference to FIG. 12. FIG. 12 is a conceptual diagram illustrating a method of synthesizing signatures at each measurement timing i and a method of verifying a resulting signature. Here, the measurement values described below are assumed to be quantized measurement values.

First, the measurement device 100 performs the first measurement in case of i=1. The first measurement is assumed to obtain a measurement value A. As previously described for S414, a distributed signature "M(1)" is therefore "$A^{d(1)} \mod n$". Here, in the distributed-signature synthesis at S415, three distributed signatures, which are this distributed signature "M(1)" in addition to "M(−1)=0" and "M(0)=0" of initialization, are synthesized together. In this case, since a value of the base is different depending on the distributed signatures in the distributed-signature synthesis (a base of M(−1) and M(0) is "0" and a base of M(1) is "A"), the above verification equation (equation (5)) is not satisfied at S417. Therefore, the measurement device 100 adds 1 to the variable i to be i=2 and measures biological data again (S418→S411).

Next, the measurement device 100 performs the second measurement. Assuming that a measurement value B is obtained, a distributed signature "M(2)" is "$B^{d(2)} \mod n$". In this situation, in the distributed-signature synthesis at S415, the three distributed signatures of "$M(2) = B^{d(2)} \mod n$", "$M(1) = A^{d(1)} \mod n$", and "M(0)=0" of initialization are synthesized together, by setting the distributed signature "M(2)" as a criterion. In the situation, since the three measurement values "B", "A", and "0" are not the same values, a value of the base is different depending on the distributed signatures in the distributed-signature synthesis. Therefore the above verification equation (equation (5)) is not satisfied at S417. Therefore, the measurement device 100 adds 1 to the variable i to be i=3 and measures biological data again (S418→S411).

Next, the measurement device 100 performs the third measurement. Assuming that a measurement value C is obtained, a distributed signature "M(3)" is "$C^{d(3)} \mod n$". In this situation, in the distributed-signature synthesis at S415, the three distributed signatures of "$M(3) = C^{d(3)} \mod n$", "$M(2) = B^{d(2)} \mod n$", and "$M(1) = A^{d(1)} \mod n$" are synthesized together, by setting the distributed signature "M(3)" as a criterion. In the situation, since the three measurement values "C", "B", and "A" are not the same values, a value of the base is different depending on the distributed signatures in the distributed-signature synthesis. Therefore, the above verification equation (equation (5)) is not satisfied at S417. Therefore, the measurement device 100 adds 1 to the variable i to be i=4 and measures biological data again (S418→S411).

Next, the measurement device 100 performs the fourth measurement. Assuming that a measurement value D is obtained, a distributed signature "M(4)" is "$D^{d(4)}$ mod n". In this situation, in the distributed-signature synthesis at S415, the three distributed signatures of "M(4)=$D^{d(4)}$ mod n", "M(3)=$C^{d(3)}$ mod n", "M(2)=$B^{d(2)}$ mod n" are synthesized together, by setting the distributed signature "M(4)" as a criterion. In the situation, since the three measurement values "D", "C", and "B" are not the same values, a value of the base is different depending on the distributed signatures in the distributed-signature synthesis. Therefore, the above verification equation (equation (5)) is not satisfied at S417. Therefore, the measurement device 100 adds 1 to the variable i to be i=5 and measures biological data again (S418→S411).

Next, the measurement device 100 performs the fifth measurement. Assuming that a measurement value D is obtained, a distributed signature "M(5)" is "$D^{d(5)}$ mod n". In this situation, in the distributed-signature synthesis at S415, the three distributed signatures of "M(5)=$D^{d(5)}$ mod n", "M(4)=$D^{d(4)}$ mod n", and "M(3)=$C^{d(3)}$ mod n" are synthesized together, by setting the distributed signature "M(5)" as a criterion. In the situation, since the three measurement values "D", "D", and "C" are not the same values, a value of the base is different depending on the distributed signatures in the distributed-signature synthesis. Therefore, the above verification equation (equation (5)) is not satisfied at S417. Therefore, the measurement device 100 adds 1 to the variable i to be i=6 and measures biological data again (S418→S411).

Next, the measurement device 100 performs the sixth measurement. Assuming that a measurement value D is obtained, a distributed signature "M(6)" is "$D^{d(6)}$ mod n". In this situation, in the distributed-signature synthesis at S415, the three distributed signatures of "M(6)=$D^{d(6)}$ mod n", "M(5)=$D^{d(5)}$ mod n", and "M(4)=$D^{d(4)}$ mod n" are synthesized together, by setting the distributed signature "M(6)" as a criterion. In this case, the three measurement values are the same "D". Therefore, a value of the base is the same for the distributed signatures in the synthesis, and the exponent reconstructs a signature generation key d. Thereby, the verification equation (equation (5)) is satisfied at S417. As a result, in this situation, the measurement device 100 completes the measurement, and transmits the eventual measurement value "D" and the corresponding signature "$D^d$ mod n" to the server 200. Here, the measurement value transmitted by the measurement device 100 to the server 200 may not yet be quantized, instead of a quantized measurement value.

According to the first embodiment, the measurement device 100 synthesizes distributed signatures generated a predetermined consecutive number of times to reconstruct a signature. Thereby, it is possible to determine that biological data is measured in the situation where the user is kept in rest state.

Figure 13:
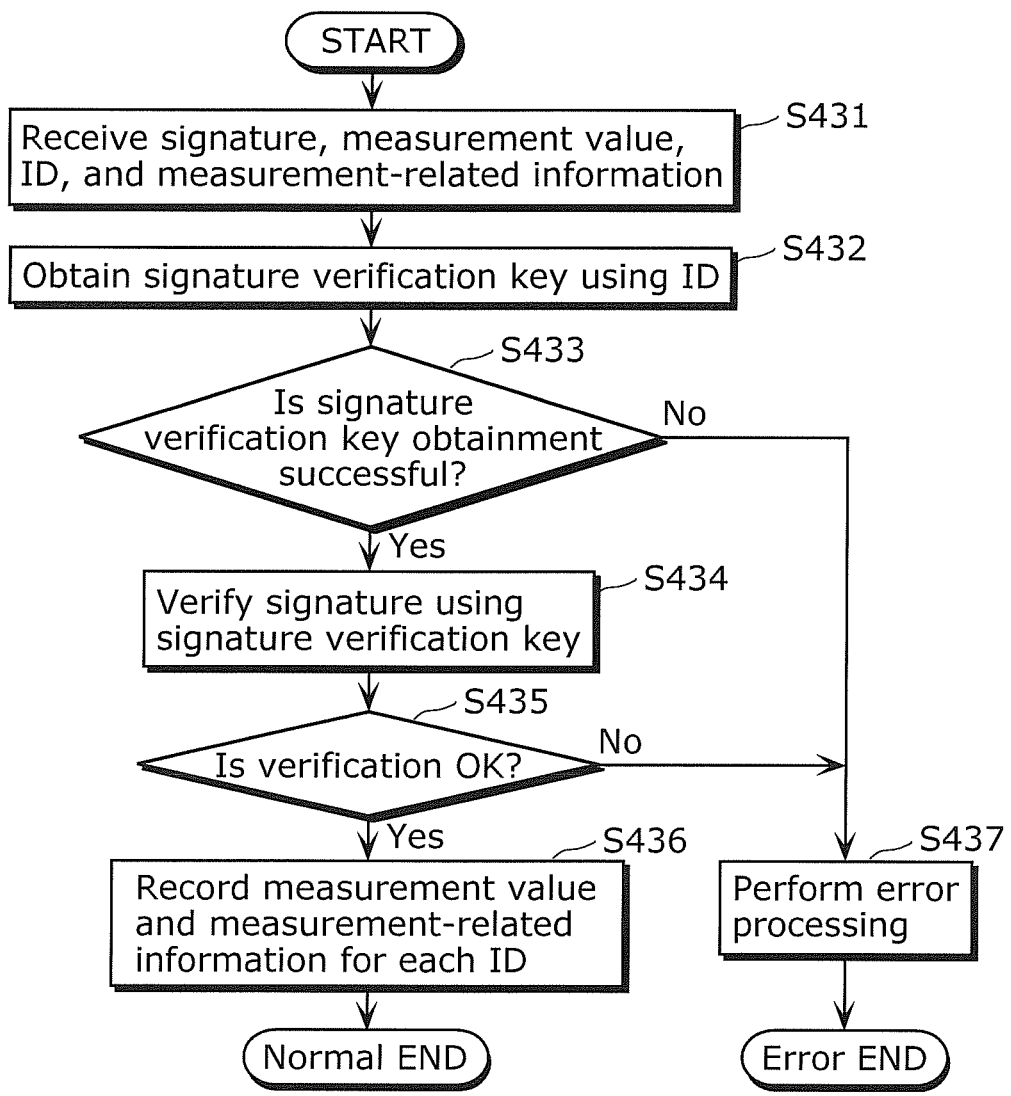
FIG. 13 is a flowchart of step S403 in FIG. 8.

FIG. 13 is a flowchart of step S403 in FIG. 8. In the step, the server 200 receives a measurement value and a signature from the measurement device 100, and verifies the received signature. If the signature is correct, the server 200 stores the received measurement value to the measurement value storage unit 207.

First, the receiving unit 203 receives data in a predetermined format (FIG. 11) which includes a measurement value, a signature, ID, and measurement-related information (S431).

Next, from the signature verification key storage unit 204, the signature verification key obtainment unit obtains a signature verification key e associated with the received ID (S432). For example, if the ID received from the measurement device 100 is "12345", the signature verification key obtainment unit 205 obtains the signature verification key "54321" from the signature verification key storage unit 204 illustrated in FIG. 5. Here, the signature verification key e is previously stored into the signature verification key storage unit 204 in the initialization (S705) described with reference FIG. 7.

Next, the signature verification key obtainment unit 205 determines whether or not the signature verification key e associated with the ID can be obtained (S433). If the signature verification key e cannot be obtained (No at S433), then the server 200 performs error processing (S437). For example, the server 200 can display on a display unit the fact that the signature verification key cannot be obtained.

On the other hand, if the signature verification key e associated with the ID can be obtained (Yes at S433), then the signature confirmation unit 206 verifies the signature using the signature verification key e (S434), thereby confirming whether or not the signature satisfies the above verification equation (equation (5)) (S435). If the signature does not satisfy the verification equation (equation (5)) (No at S435), then the server 200 performs error processing (S437). For example, the server 200 can display on the display unit the fact that the signature does not satisfy the predetermined verification equation.

If the signature satisfies the above verification equation (equation (5)) (Yes at S435), then the signature confirmation unit 206 determines that the signature is correct and therefore records the measurement value and the measurement-related information in association with the ID onto the measurement value storage unit 207 (S436). For example, in the case of FIG. 6, onto the measurement value storage unit 207, the server 200 records a measurement value of pulse and measurement date/time in association with each ID, for each of measurement start instructions of two measurement processes (for example, two processes of 9 o'clock and 12 o'clock) to the measurement device 100 having the ID "12345". The signature may be also stored.

According to the first embodiment, the measurement device 100 determines, based on a predetermined key sharing scheme, whether or not biological data is measured in user's rest state. The measurement device 100 also reconstructs a signature indicating that the biological data is measured in user's rest state. Thereby, the measurement device 100 does not need to have a structure for detecting a rest state, independent from a structure of generating a signature. As a result, the rest state detection is integrated with the signature generation. Therefore, it is possible to simplify a structure to determine whether or not biological data is measured in user's rest state.

Moreover, if the reconstructed signature is not correct, it means that measurement values of pieces of biological data are different depending on measurement times. It is thereby determined that the pieces of biological data is measured in unrest state of the user. As a result, it is possible to easily eliminate the biological data measured in user's unrest state.

Second Embodiment

In the first embodiment, the measurement device 100 determines whether or not the user is in rest state, by using biological data measures as an actual objective. For example, if the biological data is pulse or the like, the measurement values are constant during user's rest state, even having a predetermined difference range, such as "90", "89", "91", . . . . Therefore, the measurement values are quantized to eliminate the difference to be constant values. As a result, the measurement device 100 can determine whether or not the user is in rest state, using the measurement values of pulse which are an actual objective to be measured. For example, the measurement value of 89, the measurement value of 90, and the measurement value of 91 are quantized to be a measurement value 90, thereby eliminating the difference among the values.

Here, if the biological data is blood pressure, for example, the measurement value consists of both upper and lower values, such as a lower value of "70" and an upper value of "120". In the above situation, the determination as to whether the user is in rest state should be performed using not only one of the upper and lower values, but using each of them.

In order to address the above, in the second embodiment, if an actual objective to be measured is biological data such as blood pressure, measurement for the actual objective is performed in parallel with measurement of other biological data, such as pulse, which has one measurement value to allow the rest state determination to be made. Thereby, the measurement device detects whether or not the user is in rest state. In the second embodiment, in the situation where it is complicated to use a kind of biological data that is an actual objective to be measured in order to determine whether or not the user is in rest state, the measurement device can use a different kind of biological data to generate a signature indicating that the user is rest state. The second embodiment is also useful in the situation where the biological data does not have steady values such as electrocardiogram, in addition to the situation of blood pressure.

A structure of a biological data management system employing a measurement device and a method of controlling the measurement device according to the second embodiment differs from the structure of the biological data management system according to the first embodiment illustrated in FIG. 2 in that the measurement device 100 and the server 200 are replaced by a measurement device 100B and a server 200B, respectively.

Figure 14:
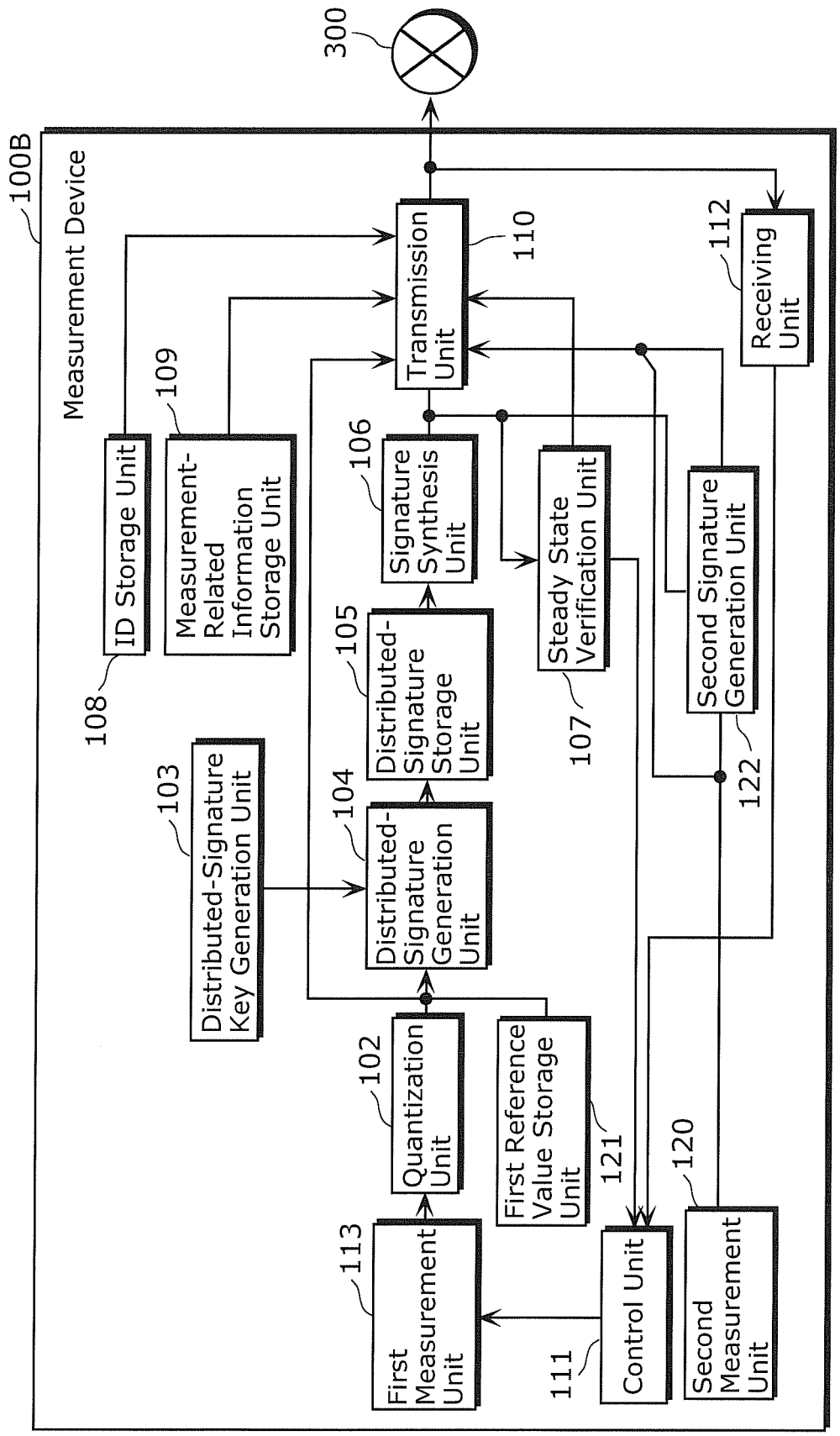
FIG. 14 is a block diagram illustrating an internal structure of the measurement device according to a second embodiment of the present invention.

FIG. 14 is a block diagram illustrating an internal structure of the measurement device 100B according to the second embodiment of the present invention. In the second embodiment, the measurement device 100B measures two kinds of biological data in parallel. More specifically, the measurement device 100B measures two kinds of biological data which are (a) biological data to be used to determine whether or not the user is in rest state and (b) biological data to be measured as an actual objective. In the following description, the biological data to be used to determine whether or not the user is in rest state is referred to as "first biological data", and the biological data to be measured as an actual objective is referred to as "second biological data". The second embodiment differs from the first embodiment in that a measurement value of the first biological data (hereinafter, referred to as a "first measurement value"), which has been measured in user's rest state, is previously set to be a first reference value (this first reference value is referred to as "D"), and it is thereby determine whether the user is in rest state if each of first measurement values measured a predetermined number of times is steady, namely, equal to the set value.

Using the secret sharing scheme described in the first embodiment, the measurement device 100B detects, based on first measurement values, that the user is in rest state, and thereby generates a first signature indicating that the user is in rest state. Then, using the first signature as a signature generation key for the second biological data (hereinafter, referred to as a "second signature generation key"), the measurement device 100B signs a measurement value of the second biological data (hereinafter, referred to as a "second measurement value"). Thereby, the measurement device 100B generates a second signature indicating that the second biological data is measured in the user's rest state. After that, the measurement device 100B transmits the second measurement value and the second signature to the server 200B.

The following describes each of the blocks included in the measurement device 100B.

The measurement device 100B includes the quantization unit 102, the distributed-signature key generation unit 103, the distributed-signature generation unit 104, the distributed-signature storage unit 105, the signature synthesis unit 106, the steady state verification unit 107, the ID storage unit 108, the measurement-related information storage unit 109, the transmission unit 110, the control unit 111, the receiving unit 112, a first measurement unit 113, a second measurement unit 120, a first reference value storage unit 121, and a second signature generation unit 122.

Each of the blocks from the quantization unit 102 to the measurement-related information storage unit 109 illustrated in FIG. 14 has the same function of the corresponding one described with reference to FIG. 3, so that they are not described again below.

The first measurement unit 113 measures first biological data to determine whether or not the user is in rest state. A piece of the first biological data is biological data, such as pulse, having a measurement value by which user's rest state can be detected.

The first reference value storage unit 121 holds the first reference value that is a criterion for determining whether or not a first measurement value is measured in user's rest state. The first reference value may be a measurement value of a piece of the first biological data which has previously been measured in user's rest state.

The distributed-signature generation unit 104 signs, at each measurement timing "1", a measurement value "m(i)" of a piece of biological data provided from the quantization unit 102, using a distributed-signature key "d(i)" provided from the distributed-signature key generation unit 103, thereby generating a distributed-signature "M(i)". In the second embodiment, the distributed-signature generation unit 104 previously signs a first reference value "D" using a distributed signature key "d(0)" in initialization, thereby generates a distributed signature "M(−1)" (where "M(−1)"=$D^{d(0)}$ mod n), and stores the distributed signature "M(−1)" to the distributed-signature storage unit 105.

By setting, as a criterion, the distributed signature "M(−1)" (where "M(−1)"=$D^{d(0)}$ mod n) of the first reference value "D", the signature synthesis unit 106 synthesizes the predetermined number, namely k, of distributed signatures including the target distributed signature "M(−1)" as the criterion together. In other words, when a distributed signature M(i) is generated at a measurement timing i, the signature synthesis unit 106 synthesizes k distributed signatures consisting of the target distributed signature "M(−1)" as the criterion and also k−1 distributed signatures "M(i)", "M(i−1)", "M(i−(k−2))" until "M(i)" together.

The second measurement unit 120 measures the second biological data that is an actual objective to be measured. In the second embodiment, a measurement value of the second biological data is transmitted to the server 200B.

When the signature synthesis unit 106 generates the first signature indicating that the user is in rest state, the second signature generation unit 122 signs a second measurement value using the first signature as a second signature generation key to generate a second signature indicating that the second biological data is measured in user's rest state.

The transmission unit 110 generates data in a predetermined format which includes: the second measurement value that is measured when the first signature indicating user's rest state is generated; the second signature; ID of the measurement device 100B; and the measurement-related information. Then, the transmission unit 110 transmits the data to the server 200B.

Figure 15:
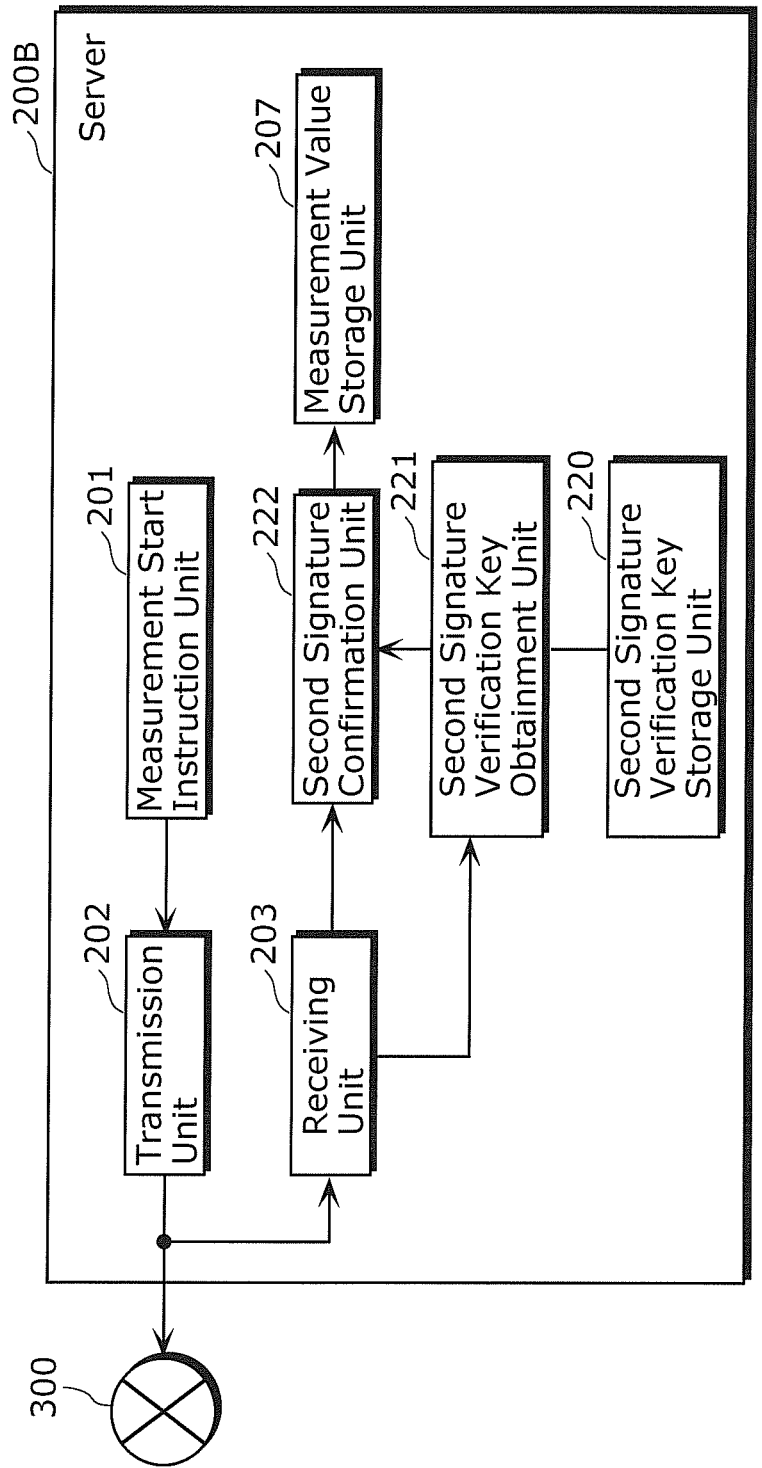
FIG. 15 is a block diagram illustrating an internal structure of a server according to the second embodiment of the present invention.

FIG. 15 is a block diagram illustrating an internal structure of the server 200B according to the second embodiment of the present invention.

The server 200B includes the measurement start instruction unit 201, the transmission unit 202, the receiving unit 203, the measurement value storage unit 207, a second signature verification key storage unit 220, a second signature verification key obtainment unit 221, and a second signature confirmation unit 222.

Each of the blocks from the measurement start instruction unit 201 to the transmission unit 202 illustrated in FIG. 15 has the same function of the corresponding one described with reference to FIG. 4, so that they are not described again below.

The receiving unit 203 receives, from the measurement device 100B, data in a predetermined format which includes a second measurement value, a second signature, ID, measurement-related information.

The second signature verification key storage unit 220 holds a second signature verification key to be used to verify the second signature gathered from the measurement device 100B, in association with ID of the measurement device 100B. The second signature verification key is previously set in the second signature verification key storage unit 220 in initialization. The second signature verification key storage unit 220 will be described in more detail later with reference to FIG. 16.

The second signature verification key obtainment unit 221 obtains, form the second signature verification key storage unit 220, the second signature verification key associated with the ID gathered from the measurement device 100B, and provides the second signature verification key to the second signature confirmation unit 222.

The second signature confirmation unit 222 verifies the second signature gathered from the measurement device 100B, by using the second signature verification key obtained from the second signature verification key storage unit 220. In more detail, the second signature confirmation unit 222 determines that the second signature is correct, if the second signature satisfies a predetermined verification equation.

The measurement value storage unit 207 holds the second measurement value and the measurement-related information in association with the ID. Here, if the second signature verified by the second signature confirmation unit 222 is correct, these pieces of information are written by the second signature confirmation unit 222 to the measurement value storage unit 207. The measurement value storage unit 207 will be described in more detail later with reference to FIG. 17.

Figure 16:
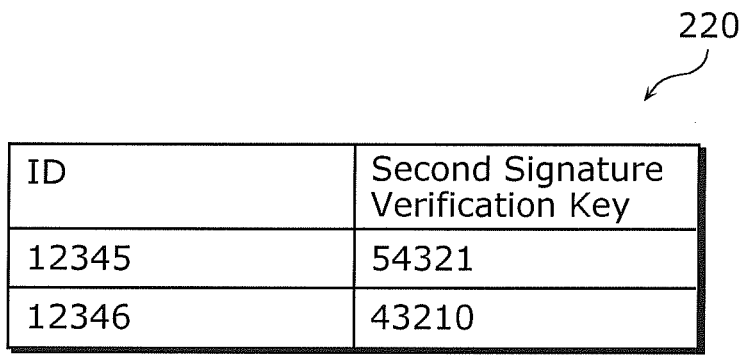
FIG. 16 is a diagram of a memory structure of a second signature verification key storage unit illustrated in FIG. 15.

FIG. 16 is a diagram of a memory structure of the second signature verification key storage unit 220 illustrated in FIG. 15. Referring to FIG. 16, the second signature verification key storage unit 220 has an item "ID" and an item "second signature verification key". The second signature verification key storage unit 220 manages the ID of the measurement device 100B and the second signature verification key in association with each other. In the item "ID", the ID for identifying the measurement device 100B is stored. In the item "second signature verification key", the second signature verification key for verifying any second signature transmitted from the measurement device 100B is stored.

For instance, in the case of FIG. 16, the second signature verification key storage unit 220 holds second signature verification keys for a measurement device 100B having ID "12345" and another measurement device 100B having ID "12346". The measurement device 100B having ID "12345" is associated with the second signature verification key "54321" while the measurement device 100B having ID "12346" is associated with the second signature verification key "43210".

Figure 17:
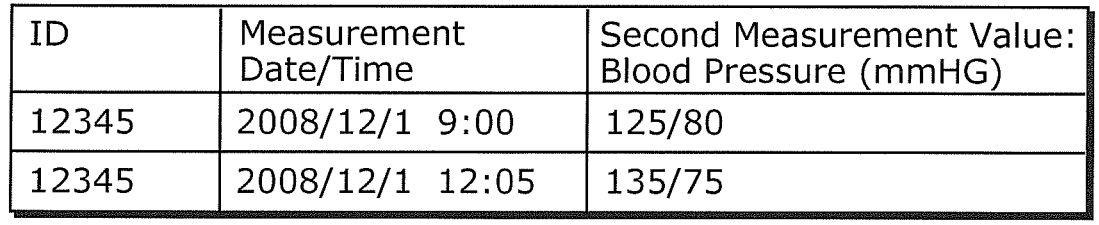
FIG. 17 is a diagram of a memory structure of a measurement value storage unit illustrated in FIG. 15.

FIG. 17 is a diagram of a memory structure of the measurement value storage unit 207 illustrated in FIG. 15. Here, it is assumed that the second biological data, which is an actual objective to be measured, is blood pressure. Referring to FIG. 17, the measurement value storage unit 207 has an item "ID", an item "measurement date/time", and an item "second measurement value: blood pressure (mmHG)". The measurement value storage unit 207 manages ID of the measurement device 100B, measurement date/time, and a measurement value of blood pressure that is the second biological data. In the item "ID", the ID for identifying the measurement device 100B is stored. In the item "measurement date/time", date and time of measuring blood pressure are recorded. In the item "second measurement value: blood pressure (mmHG)", a measurement value of blood pressure that is the second biological data is recorded.

For example, in the case of FIG. 17, the measurement value storage unit 207 records a measurement date/time and an eventual measurement value of blood pressure for each of two measurement processes performed by the measurement device 100B having ID "12345". More specifically, it is indicated that the measurement device 100B having ID "12345" measures blood pressure at "9:00 AM, Dec. 1, 2008" and that a measurement value of the measurement consists of "an upper value of 125 and a lower value of 80". Likewise, it is also indicated that the measurement device 100B having ID "12345" measures blood pressure at "12:05 AM, Dec. 1, 2008" and that a measurement value of the measurement consists of "an upper value of 135 and a lower value of 75".

The following describes the measurement device 100B having the above structure and steps of the method of controlling the measurement device 100B with reference to the figures.

Figure 18:
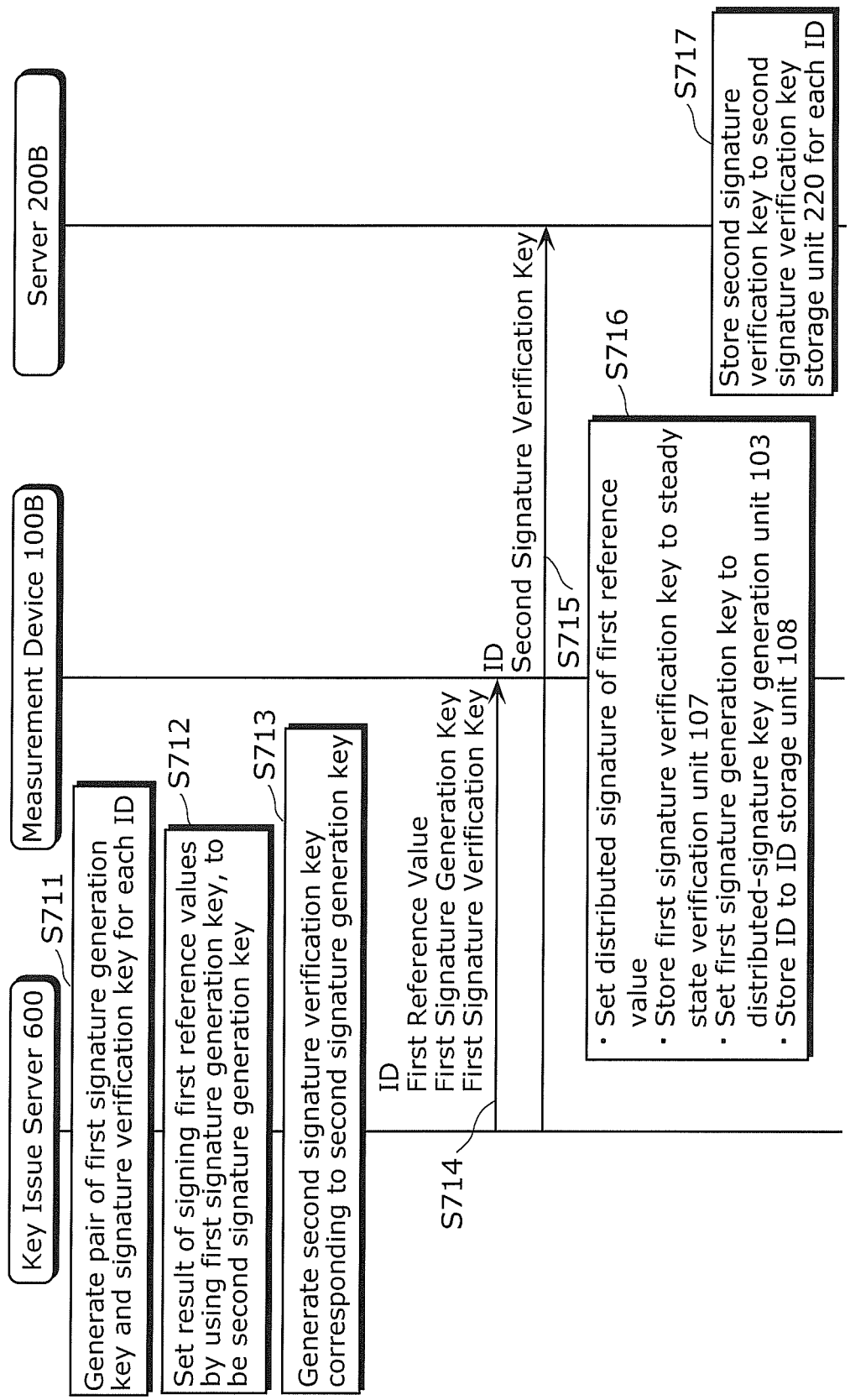
FIG. 18 is a sequence diagram illustrating processing performed by the measurement device, the server, and a key issue server in initialization in a biological data management system employing the measurement device and a method of controlling the measurement device according to the second embodiment of the present invention.

FIG. 18 is a sequence diagram illustrating processing performed by the measurement device 100B, the server 200B, and the key issue server 600 in initialization, in the biological data management system employing the measurement device 100B and the method of controlling the measurement device 100B according to the second embodiment of the present invention. In the initialization, ID, a first reference value, a first signature generation key, and a first signature verification key are set in the measurement device 100B, while the ID and a second signature verification key are set in the server 200B. The first signature generation key and the first signature verification key are used for generation and verification, respectively, of the first signature indicating user's rest state based on measurement values from the first biological data. The first signature generation key and the first signature verification key correspond to the signature generation key "d" and the signature verification key "e", respectively, which have been described in the first embodiment.

The first reference value is a value used as a criterion for determining whether or not a first measurement value is measured in user's rest state. In the second embodiment, the first reference value is set in the first reference value storage unit 121 illustrated in FIG. 14. An example of the first reference value is a measurement value of a piece of the first biological data that has previously been measured.

Previously, the key issue server 600 generates a pair of the first signature generation key "d" and the first signature verification key "e" in association with the ID of the measurement device 100B (S711). Next, the key issue server 600 signs the first reference value "D" using the first signature generation key "d" to generate a signature "$D^d$ mod n". The key issue server 600 uses the signature "$D^d$ mod n" as a second signature generation key (S712). Then, the key issue server 600 generates the second signature verification key corresponding to the second signature generation key (S713). In the second embodiment, the measurement device 100B signs the first reference value using the first signature verification key, and uses the resulting signature as the second signature verification key.

Next, the key issue server 600 distributes the ID, the first reference value "D", the first signature generation key "d", and the first signature verification key "e" to the measurement device 100B (S714), and the ID and the second signature verification key to the server 200B (S715).

In receiving the ID, the first reference value "D", the first signature generation key "d", and the first signature verification key "e" from the key issue server 600, the measurement device 100B sets the ID to the ID storage unit 108, the first reference value "D" to the first reference value storage unit 121, the first signature generation key "d" to the distributed-signature key generation unit 103, and the first signature verification key "e" to the steady state verification unit 107. The measurement device 100B previously generates a distributed signature key "d(0)" by the distributed-signature key generation unit 103, and signs the first reference value "D" using the distributed signature key "d(0)" to generate a distributed signature "M(-1)" (where M(-1)=$D^{d(0)}$mod n). Then, the distributed signature "M(-1)" (where M(-1)=$D^{d(0)}$ mod n) is set in the distributed-signature storage unit 105 (S716).

As described above, in the second embodiment, the first reference value is distributed from the key issue server 600 to the measurement device 100B, and set into the first reference value storage unit 121 illustrated in FIG. 14. The measurement device 100B previously generates a distributed signature corresponding to the first reference value, and sets this distributed signature as an initial value in the distributed-signature storage unit 105 illustrated in FIG. 14.

In receiving the ID and the second signature verification key from the key issue server 600, the server 200B sets the ID and the second signature verification key in association with each other in the second signature verification key storage unit 220 (S717). For example, in the situation where the ID has a value "12345" and the second signature verification key has a value "54321", the ID value "12345" is set in the item "ID" and the signature verification key value "54321" is set in the item "second signature verification key", in the second signature verification key storage unit 220 illustrated in FIG. 16.

Figure 19:
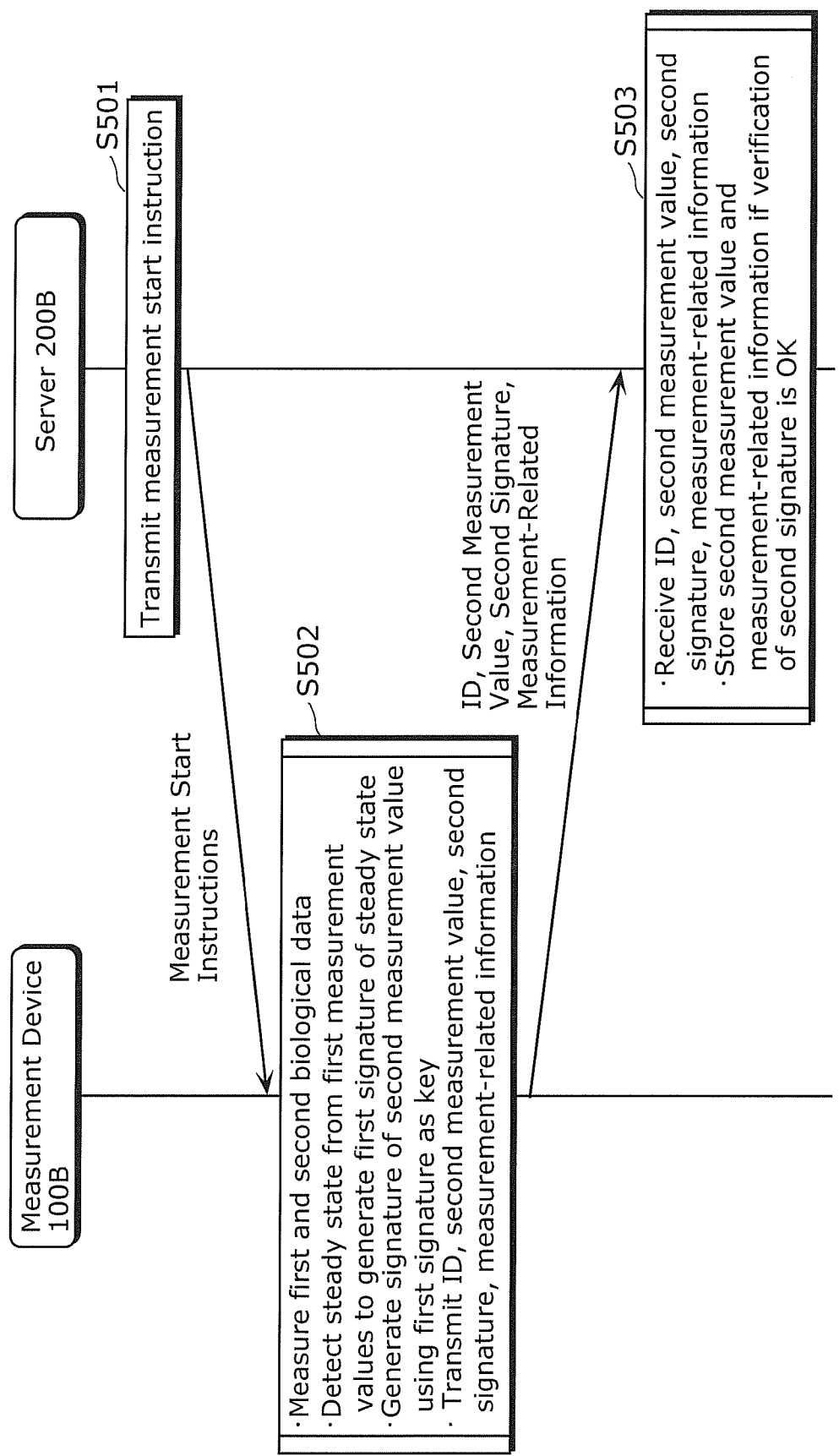
FIG. 19 is a sequence diagram illustrating processing performed by the measurement device and the server in biological data measurement in the biological data management system employing the measurement device and the method of controlling the measurement device according to the second embodiment of the present invention.

FIG. 19 is a sequence diagram illustrating processing performed by the measurement device 100B and the server 200B in measurement of the first and second biological data, in the biological data management system employing the measurement device 100B and the method of controlling the measurement device 100B according to the second embodiment of the present invention.

First, the server 200B transmits instruction for starting measurement to the measurement device 100B via the network 300 (S501).

According to the measurement start instruction, the measurement device 100B measures (a) the first biological data to be used to determine whether or not the user is in rest state and (b) the second biological data to be measured as an actual objective. The measurement device 100B detects based on the first measurement value that the user is in rest state, and thereby generates a first signature indicating that the user is in rest state. In the second embodiment, the first signature is used as the second signature generation key. Then, the measurement device 100B signs the second measurement value using the second signature key to generate the second signature indicating that the second biological data is measured in user's rest state. After that, the measurement device 110B generates data in a predetermined format which includes: the second measurement value that is measured when the first signature indicating user's rest state is generated; the second signature; the ID of the measurement device 100B, and the measurement-related information. Then, the measurement device 100B transmits the data to the server 200B (S502). The step S502 will be described in more detail later with reference to FIG. 20.

In receiving the second measurement value, the second signature, the ID, and the measurement-related information, the server 200B verifies whether or not the second signature is correct, using the second signature verification key. If the second signature is correct, then the server 200B stores the second measurement value and the measurement-related information to the measurement value storage unit 207 (S503). The step S503 will be described in more detail later with reference to FIG. 22.

In the second embodiment, even if a piece of the second biological data, which is an actual objective to be measured, consists of plural pieces of data, such as blood pressure data consisting of an upper value and a lower value, measurement of different kind of biological data, such as pulse, having a measurement value by which user's rest state can be determined is performed in parallel with and independent from the measurement of the biological data that is an actual objective to be measured. Thereby, the measurement device 100B needs only a simple structure to determine that the user is in rest state.

In addition, even if the second biological data, which is an actual objective to be measured, is not useful to determine whether or not the user is in rest state, such as electrocardiogram data not having steady values, it is possible to determine, by using the first biological data, whether or not the second biological data is measured in user's rest state. Therefore, it is possible to determine that the second biological data is measured in user's rest state.

Figure 20:
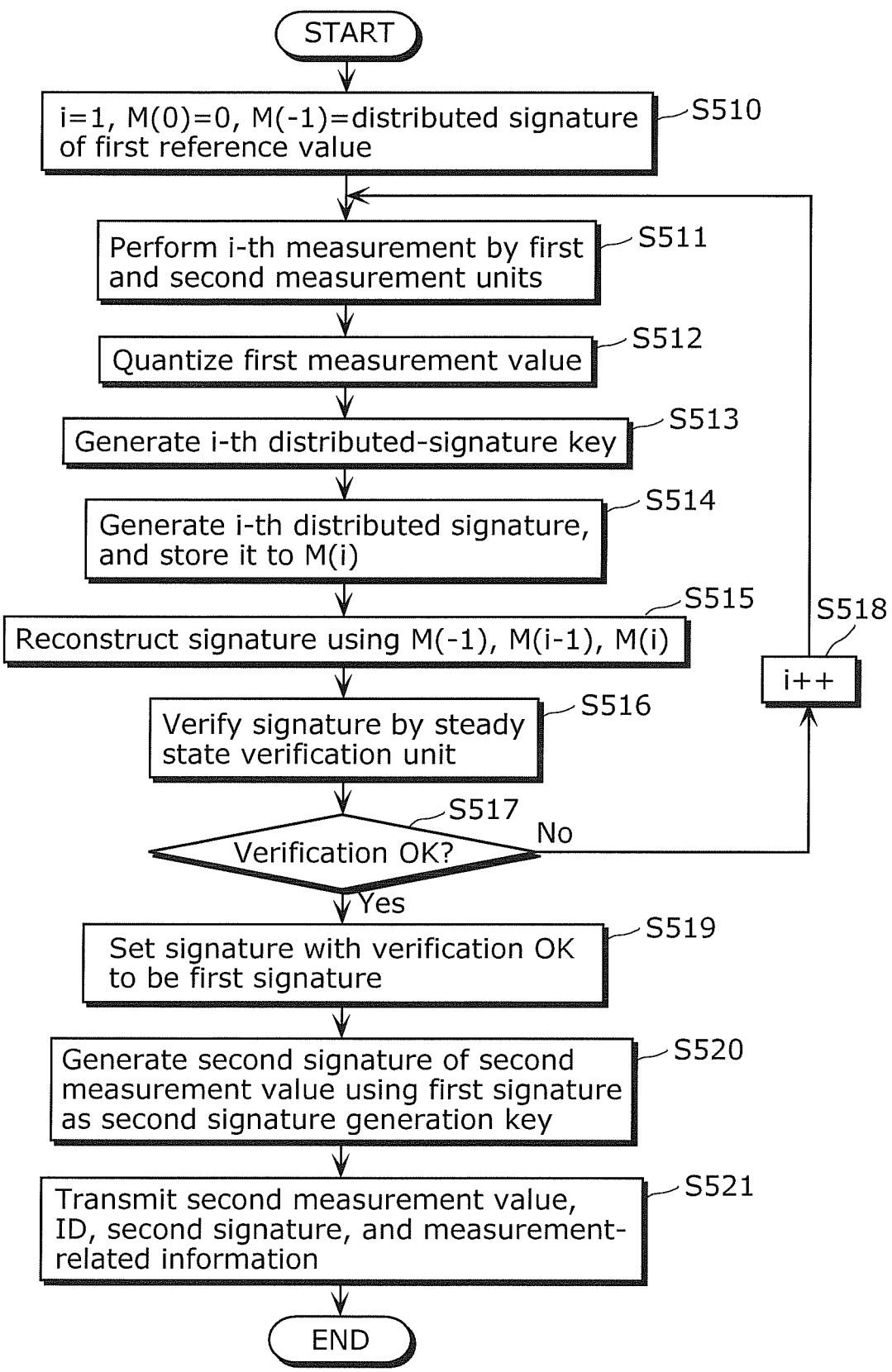
FIG. 20 is a flowchart of step S502 in FIG. 19.

FIG. 20 is a flowchart of step S502 in FIG. 19. At the step, the measurement device 100B performs measurement of the first biological data having a measurement value by which the user's rest state can be determined, in parallel with and independent from measurement of the second biological data that is an actual objective to be measured. Using the secret sharing scheme described earlier, the measurement device 100B generates, based on the first measurement value, a first signature indicating that the user is in rest state. The following describes the situation where the predetermined number of times k is "k=3". Using the first signature, the measurement device 100B generates a second signature indicating that a measurement value of the second biological data (namely, a second measurement value) is measured in user's rest state. In the following description, the first measurement value that is quantized is represented by $m_1(i)$, and the second measurement value is represented by $m_2(i)$.

In the second embodiment, when the above-described secret sharing scheme is used to detect the user's rest state based on the first measurement value, a first reference value "D" is previously signed using a distributed signature key "d(0)" to generate a distributed signature "M(-1)" (where M(-1)=$D^{d(0)}$mod n). Then, by setting the distributed signature "M(−1)" as a criterion, the predetermined number, namely three, of distributed signatures including the target distributed signature "M(−1)" as the criterion are synthesized together. In other words, when a distributed signature M(i) is generated at a measurement timing i, the signature synthesis unit 106 synthesizes three distributed signatures consisting of the target distributed signature "M(−1)" as the criterion and also two distributed signatures "M(i)" and "M(i−1)" until "M(i)", together The following describes the processing.

Previously, the control unit 111 sets the variable i to be "1" as initialization, so that "i=1". Here, as described for S716 in FIG. 19, the distributed-signature generation unit 104 previously signs the first reference value "D" using the distributed signature key "d(0)" to generate the distributed signature "M(−1)" (where M(−1)=$D^{d(0)}$ mod n). When a distributed signature "M(1)" (where M(1)=$m_1(1)^{d(1)}$ mod n) is generated after start of the measurement, the measurement device 100B cannot synthesize three distributed signatures "M(−1)", "M(0)", and "M(1)" together since the distributed signature "M(0)" does not have a value. In order to prevent such a situation, the distributed signature "M(0)" in initialization is set to be "M(0)=0" (S510). After the initialization, the measurement device 100B detects based on the first measurement value that the user is in rest state, and generate a second signature indicating that a second measurement value is measured in user's rest state.

First, the first measurement unit 113 and the second measurement unit 120 measures an i-th piece of first biological data and an i-th piece of second biological data, respectively (S511). Then, the quantization unit 102 quantized a first measurement value that is a measurement value of the i-th piece of first biological data (S512).

Next, the distributed-signature key generation unit 103 generates an i-th distributed-signature key d(i) (S513). Then, the distributed-signature generation unit 104 generates a distributed signature M(i) using the quantized first measurement value $m_1(i)$ and the distributed-signature key d(i), and stores the distributed signature M(i) to the distributed-signature storage unit 105 (S514).

Next, by setting the distributed signature "M(−1)" as a criterion, the predetermined number, namely three, of distributed signatures "M(−1)", "M(i)", and "M(i−1)" including the distributed signature "M(−1)" as the reference are synthesized together to generate a signature $S_1(i)$ (S515). Then, the steady state verification unit 107 verifies the signature $S_1(i)$ using the first signature verification key "e" (S516), thereby determining whether or not the signature $S_1(i)$ satisfies a predetermined verification equation (equation (5)) (S517). At S517, if it is determined that the signature S(i) does not satisfy the above verification equation (equation (5)), then it means that the measurement values $m_1(i)$ and $m_1(i−1)$ are not the same as the first reference value "D". In this situation (No at S517), the control unit 111 adds 1 to the variable i (S518), and the measurement device 100B measures biological data again (S518→S511).

On the other hand, at S517, if it is determined that the signature $S_1(i)$ satisfies the above verification equation (equation (5)), then it means that the measurement values $m_1(i)$ and $m_1(i−1)$ are the same as the first reference value "D". Thereby, it is possible to determined that the user is in rest state. The signature synthesis unit 106 provides the second signature generation unit 122 with the signature $S_1(i)$ as a first signature indicating the user's rest state (Yes at S517, S519).

The above-described steps S515 to S518 will be described in more detail later with reference to FIG. 21.

Next, the second signature generation unit 122 uses the first signature $S_1(i)$ as the second signature generation key. Then, the second signature generation unit 122 signs the second measurement value $m_2(i)$ using the second signature generation key, to generate a second signature $S_2(i)$ indicating that the second measurement value $m_2(i)$ is measured in user's rest state (S520).

After that, the transmission unit 110 generates data in a predetermined format which includes the second measurement value $m_2(i)$, the second signature $S_2(i)$, the ID of the measurement device 100B, and measurement-related information, and transmits the data to the server 200 (S521).

Figure 21:
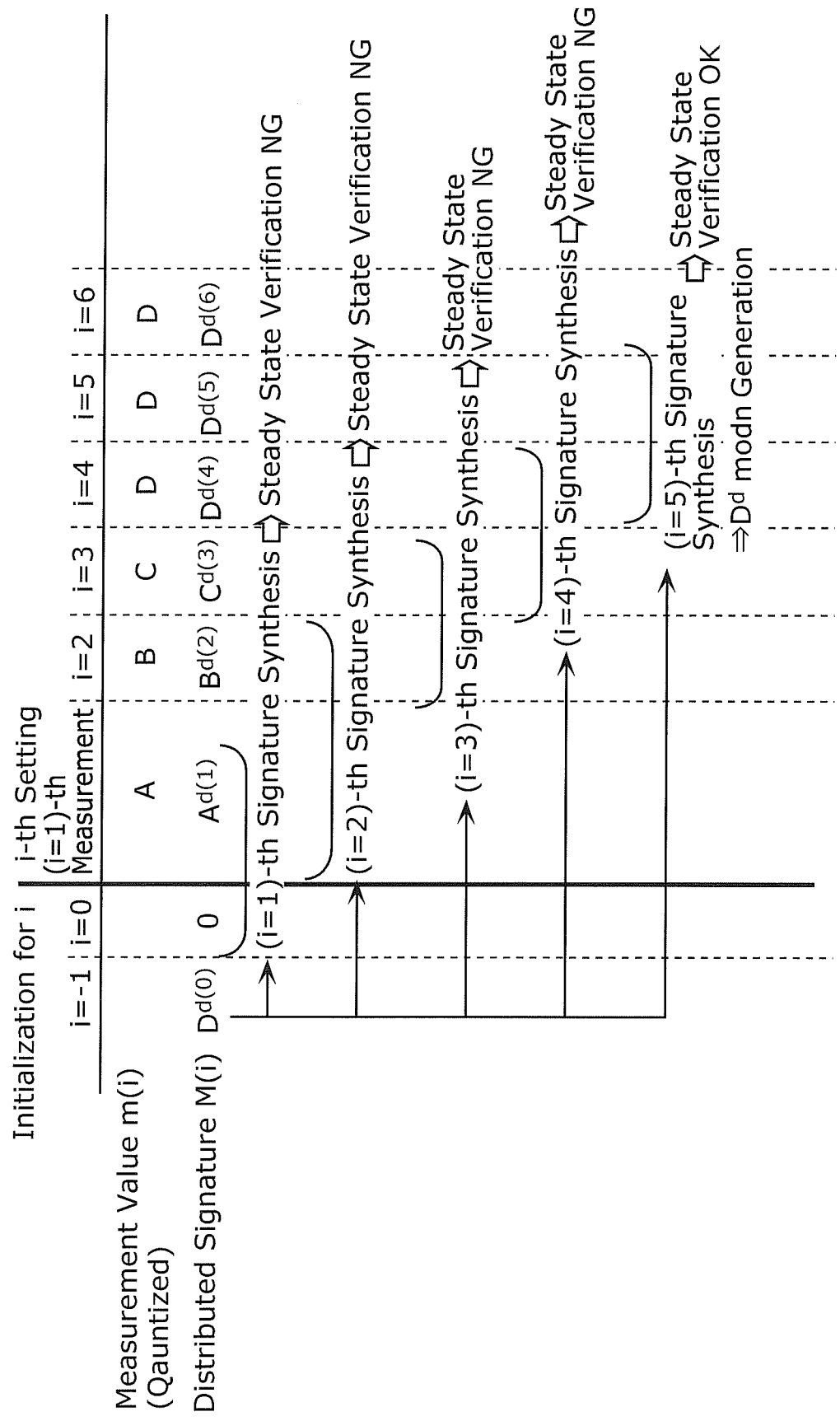
FIG. 21 is a conceptual diagram illustrating a signature synthesis method and a signature verification method used in the measurement device according to the second embodiment of the present invention.

The following describes the method of verifying the steady state from S515 to S518 in more detail with reference to FIG. 21. FIG. 21 is a conceptual diagram illustrating a method of synthesizing signatures at each measurement timing i and a method of verifying a resulting signature. The first measurement values described below are assumed to be quantized measurement values.

In the second embodiment, in initialization, the first reference value "D" is previously signed using the distributed signature key "d(0)" to set the distributed signature "M(−1)" (where M(−1)=$D^{d(0)}$ mod n). Then, when the distributed signature "M(i)" (where M(i)=$m_1(i)^{d(i)}$ mod n) is generated from the first measurement value $m_1(i)$ and the distributed-signature key "d(i)" at the measurement timing i, the signature synthesis unit 106 synthesizes, by setting the distributed signature "M(−1)" as a criterion, three distributed signatures consisting of the distributed signatures "M(i)" and "M(i−1)" and also the reference distributed signature "M(−1)" together.

First, the measurement device 100B performs the first measurement in case of i=1. Assuming that a first measurement value $m_1(1)$ represented by A is obtained from this first measurement, a distributed signature "M(1)" is therefore "$A^{d(1)}$ mod n". Here, in the distributed-signature synthesis at S515, three distributed signatures, which are this criterion distributed signature "M(−1)=$D^{d(0)}$ mod n" in addition to distributed signatures "M(1)=$A^{d(1)}$ mod n" and "M(0)=0", are synthesized together. In this situation, when the criterion first reference value "D" is chronologically compared to the initial value "0" and the first measurement value "A" obtained from the first measurement, the first reference value "D" is not the same as the two measurement values "0" and "A". Therefore, since the a value of the base is different depending on the distributed signatures values in the distributed-signature synthesis, the above verification equation (equation (5)) is not satisfied at S517. Therefore, the measurement device 100B adds 1 to the variable i to be i=2 and measures biological data again (S518→S511).

Next, the measurement device 100B performs the second measurement in case of i=2. Assuming that a first measurement value $m_1(2)$ represented by B is obtained from this second measurement, a distributed signature "M(2)" is therefore "$B^{d(2)}$ mod n". Here, in the distributed-signature synthesis at S515, three distributed signatures, which are this criterion distributed signature "M(−1)=$D^{d(0)}$ mod n" in addition to distributed signatures "M(2)=$B^{d(2)}$ mod n" and "M(1)=$A^{d(1)}$ mod n", are synthesized together. In this situation, when the criterion first reference value "D" is chronologically compared to the first measurement value "A" obtained from the first measurement and the first measurement value "B" obtained from the second measurement, the first reference value "D" is not the same as the two measurement values "A" and "B". Therefore, since a value of the base is different depending on the distributed signatures in the distributed-signature synthesis, the above verification equation (equation (5)) is not satisfied at S517. Therefore, the measurement device 100B adds 1 to the variable i to be i=3 and measures biological data again (S518→S511).

Next, the measurement device 100B performs the third measurement in case of i=3. Assuming that a first measurement value $m_1(3)$ represented by C is obtained from this third measurement, a distributed signature "M(3)" is therefore "$C^{d(3)}$mod n". Here, in the distributed-signature synthesis at S515, three distributed signatures, which are this criterion distributed signature "$M(-1)=D^{d(0)}$mod n" in addition to distributed signatures "$M(3)=C^{d(3)}$mod n" and "$M(2)=B^{d(2)}$mod n", are synthesized together. In this situation, when the criterion first reference value "D" is chronologically compared to the first measurement value "B" obtained from the second measurement and the first measurement value "C" obtained from the third measurement, the first reference value "D" is not the same as the two measurement values "B" and "C". Therefore, since a value of the base is different depending on the distributed signatures in the distributed-signature synthesis, the above verification equation (equation (5)) is not satisfied at S517. Therefore, the measurement device 100B adds 1 to the variable i to be i=4 and measures biological data again (S518→S511).

Next, the measurement device 100B performs the fourth measurement in case of i=4. Assuming that a first measurement value $m_1(4)$ represented by D is obtained from this fourth measurement, a distributed signature "M(4)" is therefore "$D^{d(4)}$mod n". Here, in the distributed-signature synthesis at S515, three distributed signatures, which are this criterion distributed signature "$M(-1)=D^{d(0)}$mod n" in addition to distributed signatures "$M(4)=D^{d(4)}$mod n" and "$M(3)=C^{d(3)}$ mod n", are synthesized together. In this situation, when the criterion first reference value "D" is chronologically compared to the first measurement value "C" obtained from the third measurement and the first measurement value "D" obtained from the fourth measurement, the first reference value "D" is not the same as both of the two measurement values "C" and "D". Therefore, since a value of the base is different depending on the distributed signatures in the distributed-signature synthesis, the above verification equation (equation (5)) is not satisfied at S517. Therefore, the measurement device 100B adds 1 to the variable i to be i=5 and measures biological data again (S518→S511).

Next, the measurement device 100B performs the fifth measurement in case of i=5. Assuming that a first measurement value $m_1(5)$ represented by D is obtained from this fifth measurement, a distributed signature "M(5)" is therefore "$D^{d(5)}$mod n". Here, in the distributed-signature synthesis at S515, three distributed signatures, which are this criterion distributed signature "$M(-1)=D^{d(0)}$mod n" in addition to distributed signatures "$M(5)=D^{d(5)}$mod n" and "$M(4)=C^{d(4)}$mod n", are synthesized together. In this situation, when the criterion first reference value "D" is chronologically compared to the first measurement value "D" obtained from the fourth measurement and the first measurement value "D" obtained from the fifth measurement, the first reference value "D" is the same as both of the two measurement values "D". Therefore, a value of the base is the same among the distributed signatures in the distributed-signature synthesis, and the exponent reconstructs a signature generation key d. Thereby, the verification equation (equation (5)) is satisfied at S517. Therefore, in the situation, the measurement device 100B completes the measurement, and transmits the signature "$D^d$ mod n" as the first signature to the second signature generation unit 122.

In the second embodiment, even if biological data, which is an actual objective to be measured, consists of plural pieces of data, such as blood pressure data consisting of an upper value and a lower value, measurement of different kind of biological data, such as pulse, having a measurement value by which user's state can be determined is performed in parallel with and independent from the measurement of the biological data that is an actual objective to be measured. Thereby, the measurement device 100B needs only a simple structure to determine that the user is in rest state.

In addition, even if the second biological data, which is an actual objective to be measured, is not useful to determine whether or not the user is in rest state, such as electrocardiogram data not having steady values, it is possible to determine, by using the first biological data, whether or not the second biological data is measured in user's rest state.

Moreover, when distributed signatures resulting from measuring the first biological data a predetermined number of times are not the same as the target distributed signature as a criterion, it is not determined that a signature reconstructed from the distributed signatures is correct. Thereby, a medical institution can determine whether a measurement value of the second biological data that is an actual objective to be measured is actually measured in user's rest state. In addition, the medical institution can determine whether the user of the second biological data is the same of the user of the first biological data.

Figure 22:
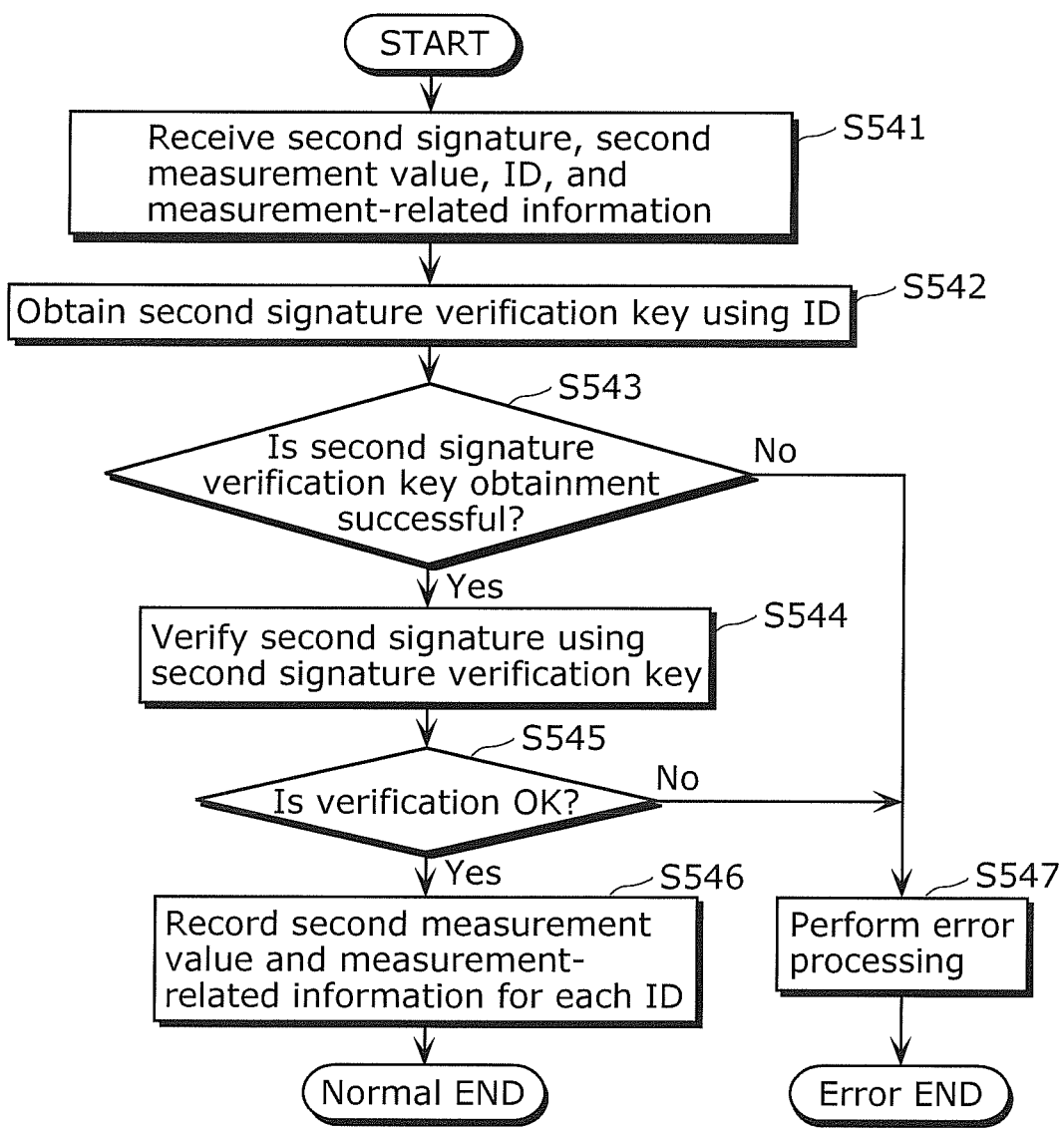
FIG. 22 is a flowchart of step S503 in FIG. 19.

FIG. 22 is a flowchart of step S503 in FIG. 19. In this processing, the server 200B receives the second measurement value and the second signature from the measurement device 100B, and verifies the received second signature. If the second signature is correct, the server 200B stores the received second measurement value to the measurement value storage unit 207.

First, the receiving unit 203 receives data in a predetermined format which includes the second measurement value, the second signature, the ID, and the measurement-related information (S541).

Next, from the second signature verification key storage unit 220, the second signature verification key obtainment unit 221 obtains a second signature verification key in associated with the received ID (S542). For example, if the ID received from the measurement device 100B is "12345", the second signature verification key obtainment unit 221 obtains the second signature verification key "54321" from the second signature verification key storage unit 220 illustrated in FIG. 16. The second signature verification key is previously generated in the key issue server 600 in the initialization described with reference to FIG. 18. The second signature verification key is set in the second signature verification key storage unit 220.

Next, the second signature verification key obtainment unit 221 determines whether or not the second signature verification key associated with the ID can be obtained (S543). If the second signature verification key cannot be obtained (No at S543), then the server 200B performs error processing (S547). For example, the server 200B can display on a display unit the fact that the second signature verification key cannot be obtained.

On the other hand, if the second signature verification key associated with the ID can be obtained (Yes at S543), then the second signature confirmation unit 222 verifies the second signature using the second signature verification key as the signature verification key e of FIG. 13 (S544), thereby confirming whether or not the second signature as S(i) satisfies the predetermined verification equation (equation (5)) in FIG. 13 (S545). If the second signature does not satisfy the predetermined verification equation (No at S545), then the server 200B performs error processing (S547). For example, the server 200B can display on the display unit the fact that the second signature does not satisfy the predetermined verification equation.

If the second signature satisfies the predetermined verification equation (equation (5)) (Yes at S545), the signature confirmation unit 206 determines that the second signature is correct, and records the second measurement value and the measurement-related information in association with the ID to the measurement value storage unit 207 (S546). For example, FIG. 17 illustrates, as an example, the situation where the second biological data that is an actual objective to be measured is blood pressure. The server 200B records a measurement value of blood pressure and measurement date/time in association with a corresponding ID on the measurement value storage unit 207, for each result of two blood pressure measurement processes performed by the measurement device 100B having ID "12345".

In the second embodiment, the server 200B previously holds the second signature verification key that is generated based on the first reference value measured in user's rest state. In receiving the second measurement value and the second signature from the measurement device 10013, the server 200B verifies the second signature using the second signature verification key.

Thereby, since the server 200B verifies the second signature using the second signature verification key generated based on the first reference value, it is possible to determine whether or not the second measurement value is measured in user's rest state. Therefore, even if biological data, which is an actual objective to be measured, consists of plural pieces of data or is not useful to determine whether or not the user is in rest state, the server 20013 can determine whether a measurement value of the biological data is measured in user's rest state.

Third Embodiment

In the second embodiment, if biological data, which is an actual objective to be measured, consists of plural pieces of data or is not useful to determine whether or not the user is in rest state, the measurement device 100B measures, in parallel, two kinds of biological data which are (a) biological data to be used to determine whether or not the user is in rest state (the first biological data) and (b) biological data that is an actual objective to be measured (the second biological data). Then, the measurement device 100B generates, from the first biological data, a first signature indicating that the user is in rest state. Using the first signature as a signature generation key for the second biological data (namely, a second signature generation key), the measurement device 100B generates a second signature indicating that a measuring value of the second biological data (namely, a second measurement value) is measured in the rest state. Thereby, the server 200B can determine that the measurement is performed while the user is in rest state.

Likewise the second embodiment, a measurement device according to the third embodiment also measures, in parallel, two kinds of biological data which are (a) biological data to be used to determine whether or not a user is in rest state (the first biological data) and (b) biological data that is an actual objective to be measured (the second biological data). Then, the measurement device according to the third embodiment generates, from measurement values of the first biological data (namely, first measurement values), a first signature indicating that the user is in rest state. In the third embodiment, the measurement device uses the first signature as an encryption key to encrypt a measurement value of the second biological data which is an actual objective to be measured. Thereby, the third embodiment can determine that biological data, which is an actual objective to be measured, is actually measured in user's rest state, and can also protect privacy of the user by assuring to keep confidential the biological data transmitted to the external server 200.

A structure of a biological data management system employing the measurement device and a method of controlling the measurement device according to the third embodiment differs from the structure of the biological data management system according to the first embodiment illustrated in FIG. 2 in that the measurement device 100 and the server 200 are replaced by a measurement device 100C and a the server 200C, respectively.

Figure 23:
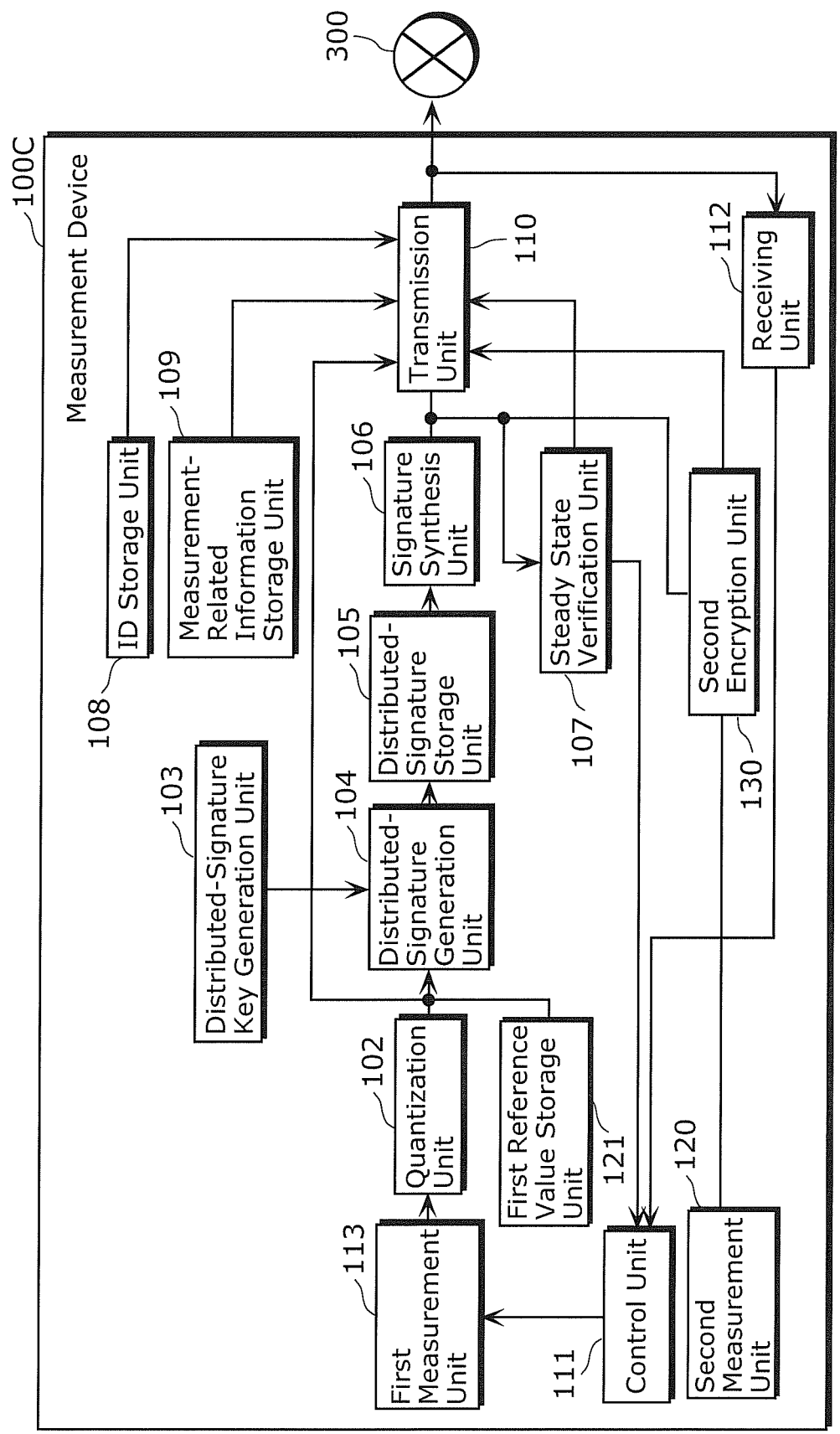
FIG. 23 is a block diagram illustrating an internal structure of the measurement device according to a third embodiment of the present invention.

FIG. 23 is a block diagram illustrating an internal structure of the measurement device 100C according to the third embodiment of the present invention.

The measurement device 100C includes the quantization unit 102, the distributed-signature key generation unit 103, the distributed-signature generation unit 104, the distributed-signature storage unit 105, the signature synthesis unit 106, the steady state verification unit 107, the ID storage unit 108, the measurement-related information storage unit 109, the transmission unit 110, the control unit 111, the receiving unit 112, the first measurement unit 113, the second measurement unit 120, the first reference value storage unit 121, and a second encryption unit 130.

The structure of the measurement device 100C differs from the structure of the measurement device 100B illustrated in FIG. 14 in that the second signature generation unit 122 is replaced by the second encryption unit 130. Therefore, each of the other blocks except the second encryption unit 130 illustrated in FIG. 23 has the same function as the corresponding one described with reference to FIG. 14, so that they are not described again below.

When the signature synthesis unit 106 generates a first signature indicating that the user is in rest state, the second encryption unit 130 encrypts a second measurement value using the first signature as an encryption key.

The transmission unit 110 generates data in a predetermined format which includes the encrypted second measurement value, ID of the measurement device 100C, and the measurement-related information, and transmits the data to the server 200C.

Figure 24:
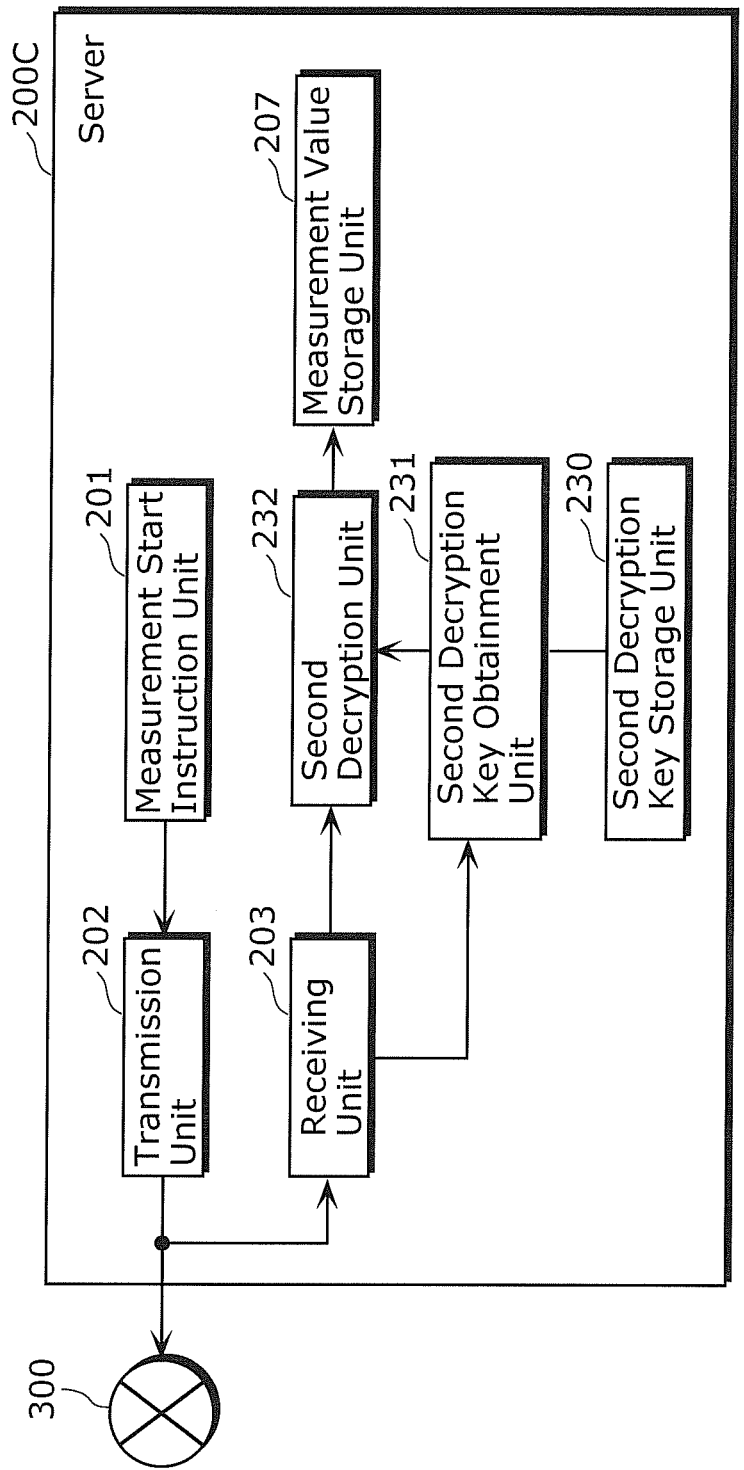
FIG. 24 is a block diagram illustrating an internal structure of a server according to an aspect of the present invention.

FIG. 24 is a block diagram illustrating an internal structure of the server 200C according to the third embodiment of the present invention.

The server 200C includes the measurement start instruction unit 201, the transmission unit 202, a receiving unit 203, a measurement value storage unit 207, a second decryption key storage unit 230, a second decryption key obtainment unit 231, and a second decryption unit 232.

Each of the blocks of the measurement start instruction unit 201 and the transmission unit 202 illustrated in FIG. 24 has the same function of the corresponding one described with reference to FIG. 15, so that they are not described again below.

The receiving unit 203 receives, from the measurement device 100C, the data in the predetermined format which includes the encrypted measurement value, the ID, and the measurement-related information.

The second decryption key storage unit 230 holds a second decryption key in association with the ID of the measurement device 100C. The second decryption key is used to verify the encrypted second signature. The second decryption key is previously set in the second decryption key storage unit 230 in initialization. The second decryption key storage unit 230 will be described in more detail later with reference to FIG. 25.

The second decryption key obtainment unit 231 obtains, from the second decryption key storage unit 230, the second decryption key associated with the ID gathered from the measurement device 100C, and provides the second decryption key to the second decryption unit 232.

The second decryption unit 232 decrypts the encrypted second measurement value using the second decryption key obtained by the second decryption key obtainment unit 231.

The measurement value storage unit 207 holds the decrypted second measurement value and the measurement-related information in association with the ID. The measurement value storage unit 207 will be described in more detail later with reference to FIG. 26.

Figure 25:
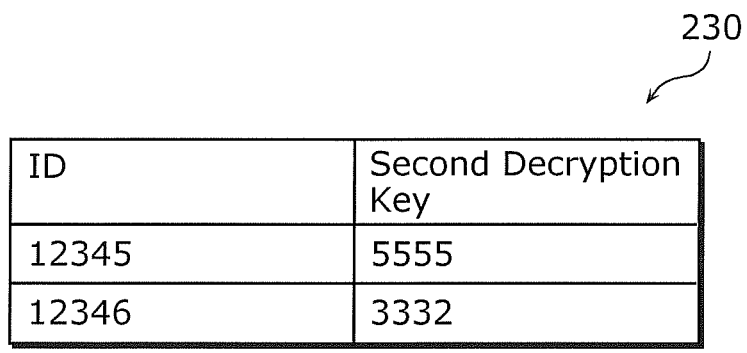
FIG. 25 is a diagram of a memory structure of a second decryption key storage unit illustrated in FIG. 24.

FIG. 25 is a diagram of a memory structure of the second decryption key storage unit 230 illustrated in FIG. 24. Referring to FIG. 25, the second decryption key storage unit 230 has an item "ID" and an item "second decryption key". The second decryption key storage unit 230 manages the ID of the measurement device 100C and the second decryption key in association with each other. In the item "ID", ID for identifying a measurement device 100C is stored. In the item "second decryption key", a second decryption key for decrypting an encrypted second measurement value is stored.

For instance, in the case of FIG. 25, the second decryption key storage unit 230 holds second decryption keys for a measurement device 100C having ID "12345" and another measurement device 100C having ID "12346". The measurement device 100C having ID "12345" is associated with the second decryption key "5555" while the measurement device 100C having ID "12346" is associated with the second decryption key "3332".

FIG. 26 is a diagram of a memory structure of the measurement value storage unit 207 illustrated in FIG. 24. Here, it is assumed that the second biological data, which is an actual objective to be measured, is electrocardiogram data. Referring to FIG. 26, the measurement value storage unit 207 has an item "ID", an item "measurement date/time", and an item "second measurement value: electrocardiogram file (file name)". The measurement value storage unit 207 manages the ID of the measurement device 100C, measurement date/time, and an electrocardiogram file that is the second biological data, in association with one another. In the item "ID", the ID for identifying the measurement device 100C is stored. In the item "measurement date/time", date and time of measuring blood pressure are recorded. In the item "second measurement value: electrocardiogram file (file name)", a file name of electrocardiogram data that is the second biological data is recorded.

For example, in the case of FIG. 26, the measurement value storage unit 207 records a measurement date/time and an electrocardiogram file name for each of two measurement processes performed by the measurement device having ID "12345". More specifically, it is indicated that the measurement device 100C having ID "12345" measures electrocardiogram at "9:00 AM, Dec. 1, 2008" and that a file name of the electrocardiogram data is "ұ12345 ұ081201 ұ0900". Likewise, it is also indicated that the measurement device 100C having ID "12345" measures electrocardiogram at "12:05 AM, Dec. 1, 2008" and that a file name of the electrocardiogram data is "ұ12345 ұ081201 ұ1205".

The following describes the measurement device 100C having the above structure and steps of the method of controlling the measurement device 100C with reference to the figures.

Figure 27:
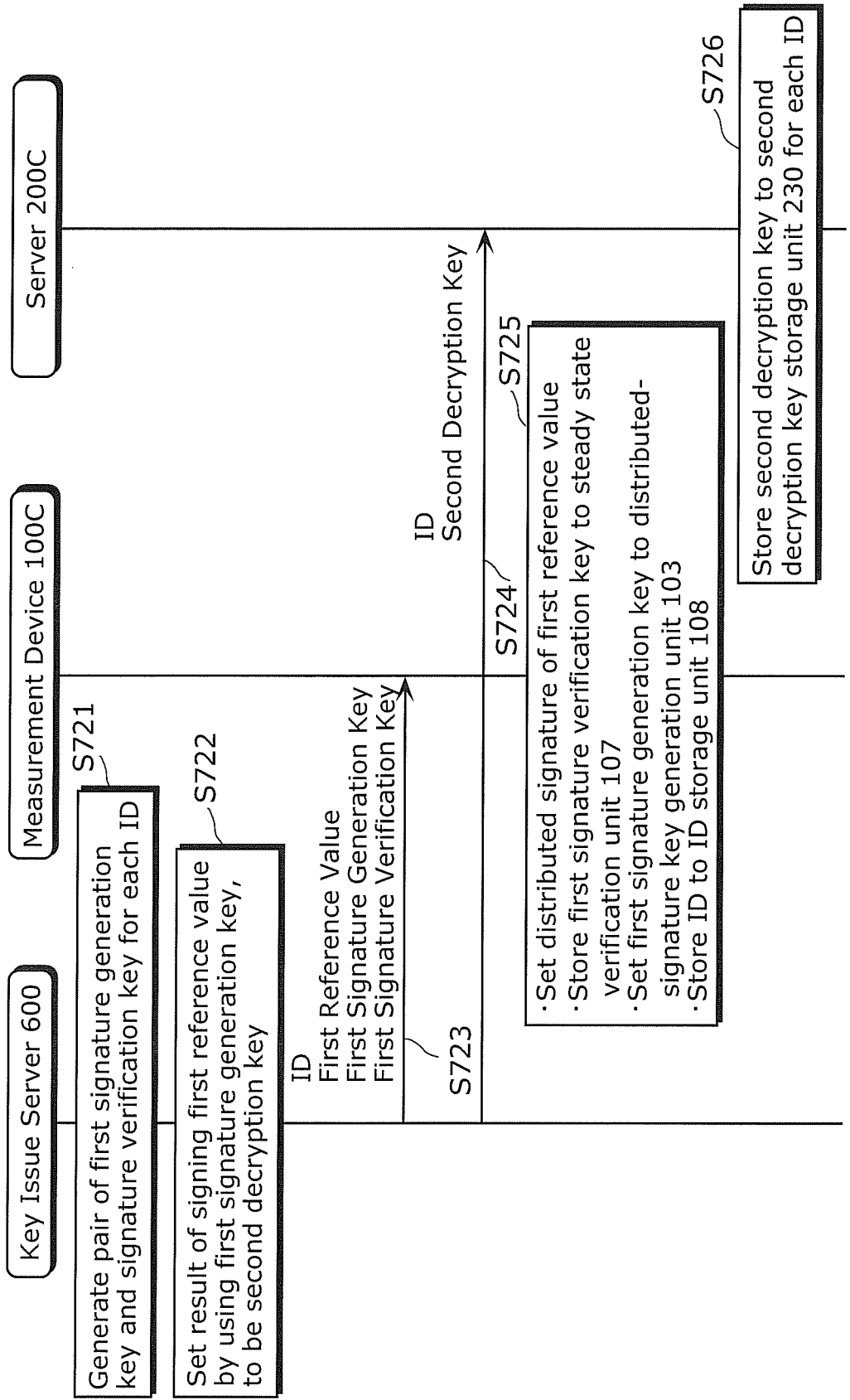
FIG. 27 is a sequence diagram illustrating processing performed by the measurement device, the server, and a key issue server in initialization in a biological data management system employing the measurement device and a method of controlling the measurement device according to the third embodiment of the present invention.

FIG. 27 is a sequence diagram illustrating processing performed by the measurement device 100C, the server 200C, and the key issue server 600 in initialization, in the biological data management system employing the measurement device 100C and the method of controlling the measurement device 100C according to the third embodiment of the present invention. In the initialization, likewise in FIG. 18, ID of the measurement device 100C, a first reference value, a first signature generation key, and a first signature verification key are set in the measurement device 100C, while the ID and a second decryption key are set in the server 200C.

Previously, the key issue server 600 generates a pair of the first signature generation key "d" and the first signature verification key "e" in association with the ID of the measurement device 100C (S721). Next, the key issue server 600 signs the first reference value "D" using the first signature generation key "d" to generate a signature "$D^d$ mod n". The key issue server 600 uses the signature "$D^d$ mod n" as a second decryption key (S722).

Next, the key issue server 600 distributes the ID, the first reference value "D", the first signature generation key "d", and the first signature verification key "e" to the measurement device 100C (S723), and the ID and the second decryption key to the server 200C (S724).

In receiving the ID, the first reference value "D", the first signature generation key "d", and the first signature verification key "e" from the key issue server 600, the measurement device 100C sets the ID to the ID storage unit 108, the first reference value "D" to the first reference value storage unit 121, the first signature generation key "d" to the distributed-signature key generation unit 103, and the first signature verification key "e" to the steady state verification unit 107. The measurement device 100C previously generates a distributed signature key "d(0)" by the distributed-signature key generation unit 103, and signs the first reference value "D" using the distributed signature key "d(0)" to generate a distributed signature "M(−1)" (where M(−1)=$D^{d(0)}$ mod n). Then, the distributed signature "M(−1)" (where M(−1)=$D^{d(0)}$ mod n) is set in the distributed-signature storage unit 105 (S725).

In receiving the ID and the second decryption key from the key issue server 600, the server 200C sets the ID and the second decryption key in association with each other to the second decryption key storage unit 230 (S726). For example, in the situation where the ID has a value "12345" and the second decryption key has a value "5555", the ID value "12345" is set in the item "ID" and the signature decryption key value "5555" is set in the item "second decryption key", in the second decryption key storage unit 230 illustrated in FIG. 25.

Figure 28:
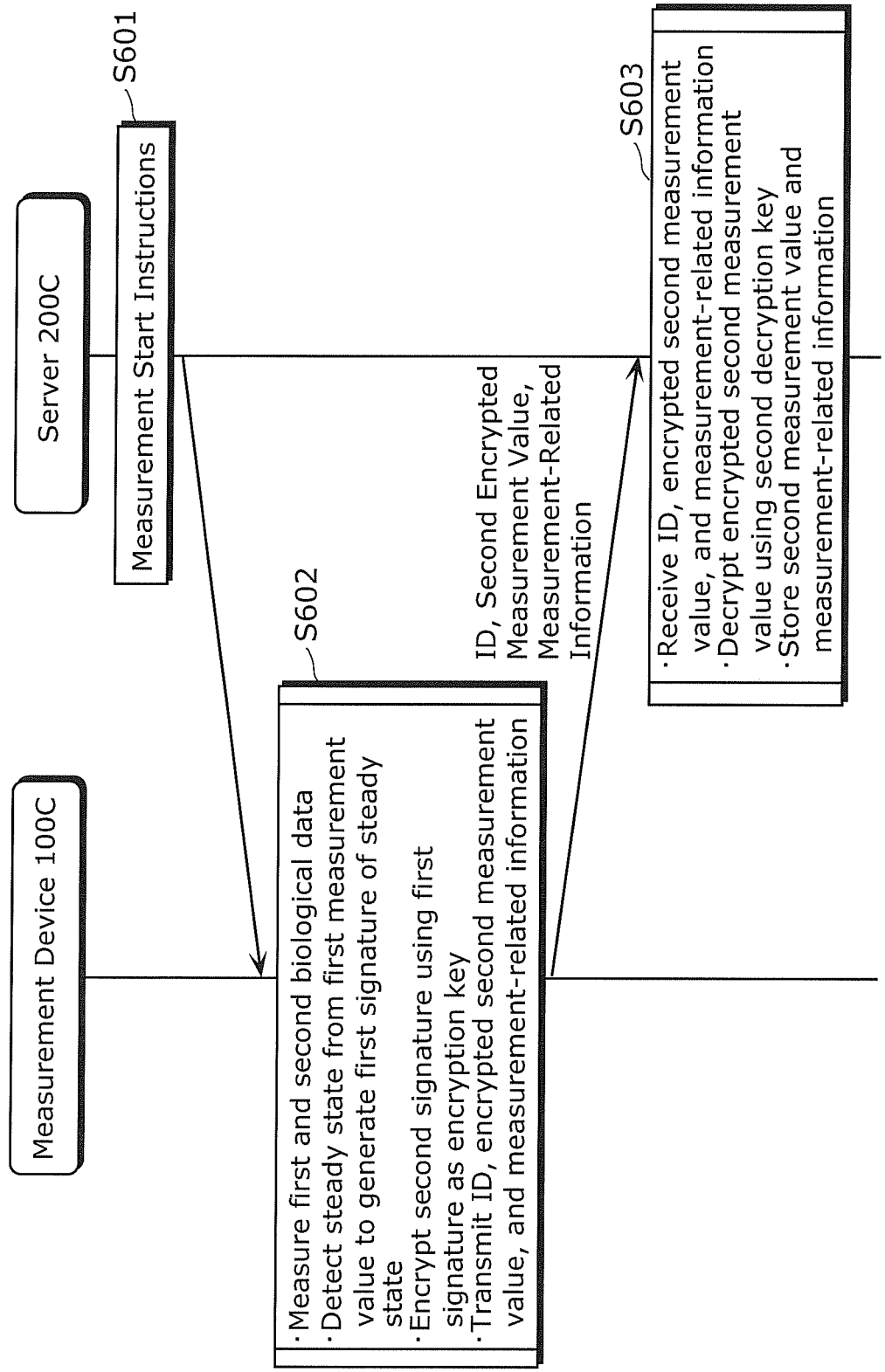
FIG. 28 is a sequence diagram illustrating processing performed by the measurement device and the server in biological data measurement in the biological data management system employing the measurement device and the method of controlling the measurement device according to the third embodiment of the present invention.

FIG. 28 is a sequence diagram illustrating processing performed by the measurement device 100C and the server 200C in measurement of the first and second biological data, in the biological data management system employing the measurement device 100C and the method of controlling the measurement device 100C according to the third embodiment of the present invention.

First, the server 200C transmits instruction for starting measurement to the measurement device 100C via the network 300 (S601).

According to the measurement start instruction, the measurement device 100C measures (a) the first biological data to be used to determine whether or not the user is in rest state and (b) the second biological data to be measures as an actual objective. The measurement device 100C detects, based on measurement values of the first biological data (namely, first measurement values), that the user is in rest state, and thereby generates a first signature indicating that the user is in rest state. Furthermore, using the first signature as an encryption key, the measurement device 100C encrypts a measurement value of the second biological data (namely, a second measurement value). After that, the measurement device 100C generates data in a predetermined format which includes the encrypted second measurement value, ID of the measurement device 100C, and measurement-related information, and transmits the data to the server 200C (S602). The step S602 will be described in more detail later with reference to FIG. 29.

In receiving the encrypted second measurement value, the ID, and the measurement-related information, the server 200C decrypts the encrypted second measurement value using a second decryption key. In addition, the server 200C stores the decrypted second measurement value and the measurement-related information to the measurement value storage unit 207 (S603). The step S603 will be described in more detail later with reference to FIG. 30.

Figure 29:
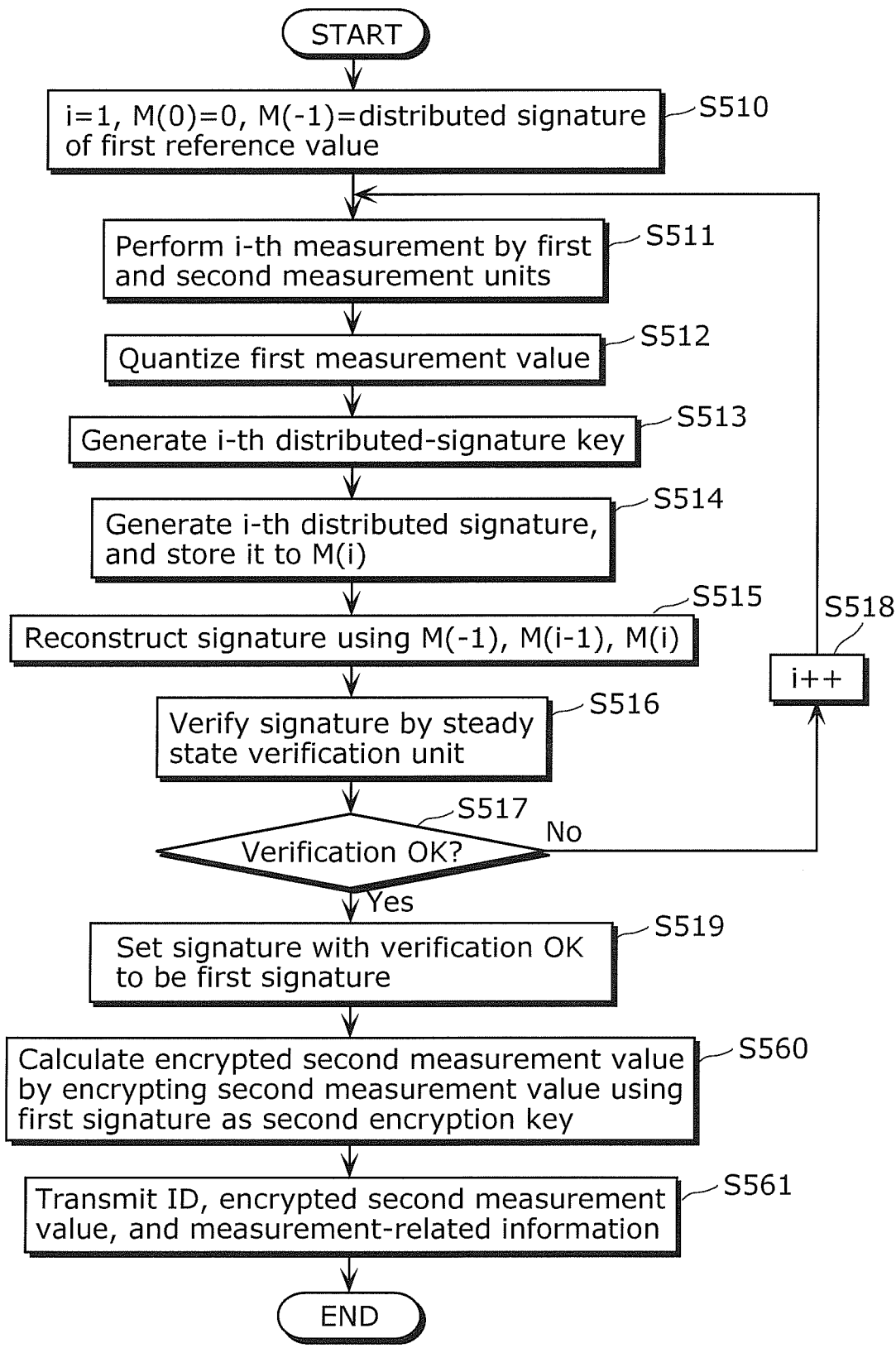
FIG. 29 is a flowchart of step S602 in FIG. 28.

FIG. 29 is a flowchart of step S602 in FIG. 28. Likewise the second embodiment (FIG. 20), in the above processing, the measurement device 100C firstly measures, in parallel, two kinds of biological data which are (a) the first biological data that is biological data to be used to determine whether or not a user is in rest state and (b) the second biological data that is biological data to be measured as an actual objective. Furthermore, the measurement device 100C generates, from first measurement values, a first signature indicating that the user is in rest state, and uses the first signature as an encryption key to encrypt a second measurement value that is an actual objective to be measured.

It should be noted that the steps from S510 to S519 in FIG. 29 are the same steps from S510 to S510 described with reference to FIG. 20, so that the same steps are not described in detail below.

Previously, likewise the processing of FIG. 20, the control unit 111 performs initialization (S510). After the initialization, the first measurement unit 113 and the second measurement unit 120 firstly measures an i-th piece of the first biological data and an i-th piece of the second biological data, respectively (S511). Then, the quantization unit 102 quantizes a first measurement value that is a measurement value of the i-th piece of the first biological data (S512). Using the secret sharing scheme described earlier, the measurement device 100C generates, based on the quantized first measurement value, a first signature indicating that the user is in rest state (S512 to S519). It should be noted that, in the processing, the method of determining based on the first measurement value whether or not the user is in rest state is the same as the method described with S513 to S518 in FIG. 20 and FIG. 21.

Next, the processing after generating a first signature at S519 is described in detail. When the first signature is generated at S519, the second encryption unit 130 encrypted a measurement value (second measurement value) of the i-th piece of the second biological data using the first signature as an encryption key. After that, the transmission unit 110 generates data in a predetermined format which includes the encrypted second measurement value, the ID of the measurement device 100C, and measurement-related information, and transmits the data to the server 200C (S561).

In the third embodiment, a first signature indicating that the user is in rest state is generated based on a first measurement value, and then used as an encryption key to encrypt a second measurement value that is an actual objective to be measured. Thereby, the third embodiment can determine whether or not biological data, which is an actual objective to be measured, is actually measured in user's rest state, and can also protect privacy of the user by assuring to keep confidential the biological data transmitted to the external server 200C.

Figure 30:
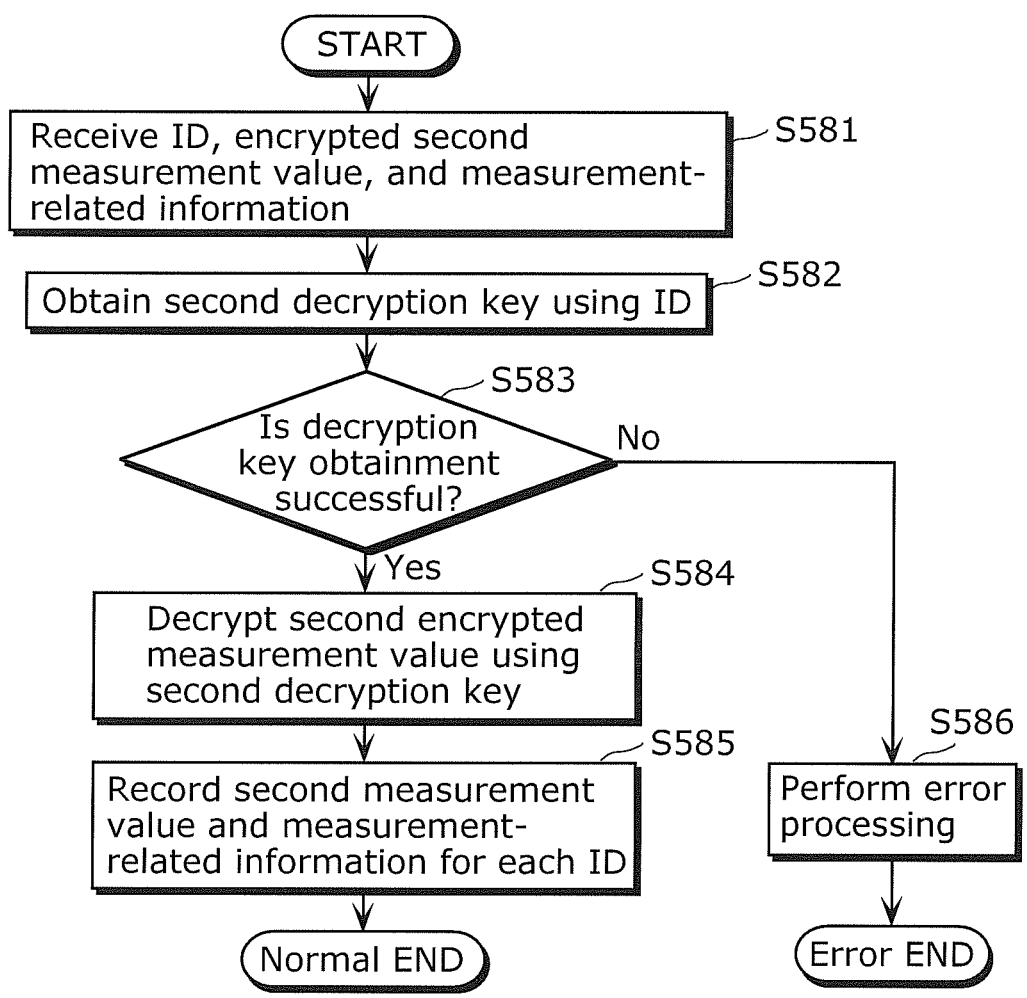
FIG. 30 is a flowchart of step S603 in FIG. 28.

FIG. 30 is a flowchart of step S603 in FIG. 28. In the processing, the server 200C receives the encrypted second measurement value from the measurement device 100C, and decrypts the encrypted second measurement value using a second decryption key.

First, the receiving unit 203 receives the data in the predetermined format which includes the encrypted second measurement value, the ID, and the measurement-related information (S581).

Next, the second decryption key obtainment unit 231 obtains, from the second decryption key storage unit 230, a second decryption key associated with the ID (S582). For example, if the ID received from the measurement device 100C is "12345", the second decryption key obtainment unit 231 obtains the second decryption key "5555" from the second decryption key storage unit 230 illustrated in FIG. 25. The second decryption key is previously generated in the key issue server 600 in the initialization described with reference to FIG. 18. The second decryption key is set into the second decryption key storage unit 230.

Next, the second decryption key obtainment unit 231 determines whether or not the second decryption key associated with the ID can be obtained (S583). If the second decryption key cannot be obtained (No at S583), then the server 200C performs error processing (S586). For example, the server 200C can display on a display unit the fact that the second decryption key cannot be obtained.

On the other hand, if the second decryption key associated with the ID can be obtained (Yes at S583), then the second decryption unit 232 decrypts the encrypted second measurement value using the second decryption key (S584). Furthermore, the second decryption unit 232 records the second measurement value and the measurement-related information in association with the corresponding ID, to the measurement value storage unit 207 (S585). For example, in the case of FIG. 26, onto the measurement value storage unit 207, the server 200C records a file name of electrocardiogram data and measurement date/time in association with a corresponding ID, for each of results of two electrocardiogram measurement processes performed by the measurement device 100C having ID "12345".

In the third embodiment, the server 200C previously holds the second decryption key that is generated based on the first reference value measured while the user is in rest state. Then, in receiving the encrypted second measurement value from the measurement device 100C, the server 200C decrypts the encrypted second measurement value using the second decryption key. Thereby, the server 200C verifies the encrypted second measurement value using the second decryption key generated based on the first reference value. As a result, the server 200C can determine whether or not the second measurement value is measured in user's rest state. In addition, the server 200C can protect privacy of the user by assuring to keep confidential the biological data transmitted from the measurement device 100C.

<Variations>

(1) It should be noted that it has been described in the first to third embodiments that the user always wears the measurement device such as a sphygmomanometer so that biological data is measured according to instructions from the server in a medical institution and eventually reliable measurement data is automatically transmitted. However, the user does not need to always wear the measurement device. In addition, the measurement data is not necessarily transmitted automatically. The user may press a transmission button to transmit the measurement data.

(2) It should also be noted that it has been described in the first to third embodiments that the measurement device starts measurement according to instructions from the server in a medical institution. But it is also possible that the measurement device is provided with a timer and thereby starts measurement every time a certain time period passes. It is also possible that there is a sensor separate from the measurement device to detect that the user leaves home, by using a Global Positioning System (GPS), for example, and starts measurement according to the detection.

(3) It should also be noted that it has been described in the second and third embodiments that the first measurement value is used to detect user's rest state when the second measurement value itself cannot be used to detect it. However, the present invention is not limited to the above. The first measurement value is used in stead of the second measurement value to detect the user's rest state, when the second measurement value measured in the rest state is to be secret from others, or when the first measurement value is appropriate to detect the rest state.

(4) It should also be noted that it has been described in the first and second embodiments that the server in a medical institute verifies a signature and thereby records a measurement value and measurement-related information. However, the received signature may be also recorded in the server. Thereby, the signature of the measurement value can be confirmed again after the recording.

(5) It should also be noted that it has been described in the first to third embodiments that the distributed-signature key generation unit calculates distributed-signature keys if each of them is needed. However, it is also possible that distributed-signature keys are previously generated and stored, and then sequentially provided to the distributed-signature key generation unit.

(6) The secret sharing scheme employed in the first to third embodiments is not limited to the two methods described earlier. Other secret sharing schemes can be adopted.

(7) It should also be noted that it has been described in the first to third embodiments that examples of the measured biological data are blood pressure, pulse, and electrocardiogram. However, the present invention is not limited to the above. For example, the biological data may be a respiration rate or a body temperature.

(8) It should also be noted that it has been described in the first to third embodiments that consecutive k measurement values as inputs are used to synthesize signatures into a signature which is used to determine whether nor not biological data is steady, in other words, determine user's rest state. However, the measurement values used in the signature synthesis is not limited to consecutive k. It is also possible that, assuming that the number of measurement processes is L, arbitrary k measurement values are retrieved from the L measurement values to perform the signature synthesis to determine user's rest state.

(9) It should also be noted that it has been described in the second and third embodiments that the first biological data is used to detect user's rest state, and to sign or encrypt the second biological data. The second biological data has been described to be data by alone which user's rest state is difficult to be detected (for example, electrocardiogram). However, the second biological data is not limited to the above and may be any.

(10) It should also be noted that it has been described in the first to third embodiments that the measurement device may notify the server of an error when measurement values are not steady in a certain time period or in a certain number of measurement processes. The notifying method may be the following.

notify only the fact that the measurement values are not steady notify the fact that the measurement values are not steady, and the measurement values (without a signature)

(11) It should also be noted in the first to third embodiments that the measurement device may alert the user when measurement values are not steady in a certain time period or in a certain number of measurement processes.

(12) It should also be noted in the first to third embodiments that a level of the quantization method employed by the quantization unit may be selected by the user. A user with relatively steady measurement values may select quantization that produces various outputs from measurement values with a small difference. On the other hand, a user with unsteady measurement values may select quantization that produces the same outputs from measurement values with a large difference. The level may be set in initialization, or may be automatically selected by entering age of the user or the like. In the above case, signature data may be added with information indicating the quantization level.

(13) It should also be noted in the first to third embodiments that the level of the quantization method employed by the quantization unit may be changed depending on the number of measurement processes. It is possible that the initial stage of the measurement employs quantization that produces various outputs from measurement values with a small difference, and when measurement results are not steady, the quantization is changed to produce the same outputs from measurement values with a large difference. In the above case, signature data may be added with information indicating the quantization level.

(14) It should also be noted that it has been described in the second and third embodiments that the first reference value is stored in the first reference value storage unit 121 and the distributed-signature generation unit 104 uses a distributed-signature key "d(0)" to perform signature distribution for the first reference value to generate a distributed signature "M(−1)". However, the distributed signature "M(−1)" may be previously stored in the first reference value storage unit 121. In the above case, it is possible that the first reference value storage unit 121 is connected to the signature synthesis unit 106 that reads the distributed signature "M(−1)" from the first reference value storage unit 121 to synthesize k distributed signatures consisting of the distributed signature "M(−1)" and k−1 distributed signatures "M(i)", "M(i−1)", . . . , "M(i−(k−2))".

(15) It should also be noted that each of the devices according to the first to third embodiments may be an independent computer program, a module embedded in an operation system, a driver called by an operation system, or an application program.

(16) It should also be noted that each of the devices according to the first to third embodiments is implemented as a computer system including a microprocessor, a Read Only Memory (ROM), a Random Access Memory (RAM), a hard disk unit, a display unit, a keyboard, and a mouse. Such a RAM or hard disk unit holds a computer program. When a microprocessor performs operations according to the computer program, each of the devices executes its functions. Here, the computer program is combinations of a plurality of instruction codes indicating instructions to a computer so as to execute predetermined functions.

(17) It should also be noted that a part or all of structural elements in each of the devices according to the first to third embodiments may be integrated into a single system Large Scale Integration (LSI). The system LSI is a super multi-function LSI that is a single chip into which a plurality of elements are integrated. More specifically, the system LSI is a computer system including a microprocessor, a ROM, a RAM, and the like. The RAM holds a computer program. When the microprocessor performs operations according to the computer program, the system LSI executes its functions.

The structural elements in each of the devices may be integrated separately, or a part or all of them may be integrated into a single chip.

Here, the integrated circuit is referred to as a system LSI, but the integrated circuit can be called an IC, a LSI, a super LSI or an ultra LSI depending on their degrees of integration. The technique of integrated circuit is not limited to the LSI, and it may be implemented as a dedicated circuit or a general-objective processor. It is also possible to use a Field Programmable Gate Array (FPGA) that can be programmed after manufacturing the LSI, or a reconfigurable processor in which connection and setting of circuit cells inside the LSI can be reconfigured.

Furthermore, if due to the progress of semiconductor technologies or their derivations, new technologies for integrated circuits appear to be replaced with the LSIs, it is, of course, possible to use such technologies to implement the functional blocks as an integrated circuit. For example, biotechnology and the like can be applied to the above implementation.

(18) It should also be noted that a part or all of the structural elements in each of the devices according to the first to third embodiments may be implemented as an Integrated Circuit (IC) card or a single module which is attachable to and removable from the device. The IC card or the module is a computer system including a microprocessor, a ROM, a RAM, and the like. The IC card or the module may include the above-described super multi-function LSI. When the microprocessor performs operations according to the computer program, the IC card or the module executes its functions. The IC card or the module may have tamper resistance.

(19) It should also be noted that the present invention may be the above-described method. The present invention may be a computer program causing a computer to execute the method, or digital signals indicating the computer program.

It should also be noted that the present invention may be a computer-readable recording medium on which the computer program or the digital signals are recorded. Examples of the computer-readable recording medium are a flexible disk, a hard disk, a Compact Disc (CD)-ROM, a magnetooptic disk (MO), a Digital Versatile Disc (DVD), a DVD-ROM, a DVD-RAM, a BD (Blue-ray™ Disc), and a semiconductor memory. The present invention may be digital signals recorded on the recording medium.

It should also be noted in the present invention that the computer program or the digital signals may be transmitted via an electric communication line, a wired or wireless communication line, a network represented by the Internet, data broadcasting, and the like.

It should also be noted that the present invention may be a computer system including a microprocessor operating according to the computer program and a memory storing the computer program.

It should also be noted that the program or the digital signals may be recorded onto the recording medium to be transferred, or may be transmitted via a network or the like, so that the program or the digital signals can be executed by a different independent computer system.

(20) It should also be noted that the above-described first to third embodiments and their variations may be combined. The disclosed embodiments are merely exemplary and do not limit the present invention. The scope of the present invention is indicated not by the above description but by the appended claims. Accordingly, all modifications are intended to be included within the same meanings and the scope of the claims.

INDUSTRIAL APPLICABILITY

The present invention can be used as a measurement device and the like to measure biological data.

NUMERICAL REFERENCES 100, 100B, 100C measurement device
101, 113 first measurement unit
102 quantization unit
103 distributed-signature key generation unit
104 distributed-signature generation unit
106 signature synthesis unit
107 steady state verification unit
120 second measurement unit
121 first reference value storage unit
122 second signature generation unit
130 second encryption unit
200, 200B, 200C server
204 signature verification key storage unit
205 signature verification key obtainment unit
206 signature confirmation unit
207 measurement value storage unit
220 second signature verification key storage unit
221 second signature verification key obtainment unit
222 second signature confirmation unit
230 second decryption key storage unit
231 second decryption key obtainment unit
232 second decryption unit
600 key issue server

The invention claimed is:
1. A measurement device comprising:
a first measurement unit configured to measure first biological data at least k times, where k≥2, to obtain any k first measurement values;
a distributed-signature generation unit configured to execute signature operations for the k first measurement values using any various k distributed-signature keys, respectively, to generate k distributed signatures, the k distributed-signature keys being capable of reconstructing a signature generation key only when all of the k distributed-signature keys are available;
a signature synthesis unit configured to synthesize the k distributed signatures together to reconstruct a signature; and
a steady state verification unit configured to verify, using a signature verification key corresponding to the signature generation key, whether or not the signature reconstructed by said signature synthesis unit is correct, where the correctness of the signature means that the k first measurement values are same values,
wherein a result of a multiplication of the signature generation key and the signature verification key is a predetermined value,
each of the signature operations is exponentiation where a corresponding one of the k distributed-signature keys or the signature generation key is an exponent, the signature generation key is generated by summing values of respective multiplications of the k distributed-signature keys by respective predetermined coefficients, said distributed-signature generation unit is configured to generate the k distributed signatures by executing the exponentiation for the k first measurement values, respectively, a base of the exponentiation being each of the k first measurement values, and an exponent of the exponentiation being a distributed-signature key corresponding to the each of the k first measurement values among the k distributed-signature keys, said signature synthesis unit is configured to calculate the signature by raising the k distributed signatures respectively to power of the respective predetermined coefficients to generate k exponentiation results, and multiplying the k exponentiation results together, and said steady state verification unit is configured to determine by the verification that the signature reconstructed by said signature synthesis unit is correct, when a predetermined verification equation is satisfied, a left-hand side of the predetermined verification equation being exponentiation where the signature is a base and the signature verification key is an exponent, and a right-hand side of the predetermined verification equation being a target first measurement value from among the k first measurement values.

2. The measurement device according to claim 1, further comprising
a transmission unit configured to transmit, to an external server, one of the k first measurement values together with the signature reconstructed by said signature synthesis unit, when said steady state verification unit determines by the verification that the signature is correct.

3. The measurement device according to claim 1, further comprising
a second measurement unit configured to measure second biological data to obtain a second measurement value, the second biological data being different from the first biological data measured by said first measurement unit and being measured in parallel to the measurement of the first biological data,
wherein said steady state verification unit is further configured to permit the second measurement value obtained by said second measurement unit to be transmitted outside, when said steady state verification unit determines by the verification that the signature reconstructed by said signature synthesis unit is correct.

4. The measurement device according to claim 3, further comprising
a first reference value storage unit configured to store, as a reference value, a criterion value to be used as a criterion for the k first measurement values,
wherein said distributed-signature generation unit is configured to generate the k distributed signatures by executing the signature operations for the reference value and (k−1) first measurement values among the k first measurement values using the k distributed-signature keys, respectively.

5. The measurement device according to claim 3, further comprising:
a second signature generation unit configured to generate a signature of the second measurement value using, as a signature generation key, the signature reconstructed by said signature synthesis unit; and
a transmission unit configured to transmit the second measurement value together with the signature of the second measurement value to an external server, when said steady state verification unit permits the second measurement value to be transmitted outside.

6. The measurement device according to claim 3, further comprising:
a second encryption unit configured to encrypt the second measurement value using, as an encryption key, the signature reconstructed by said signature synthesis unit; and
a transmission unit configured to transmit the second measurement value encrypted by said second encryption unit to an external server, when said steady state verification unit permits the second measurement value to be transmitted outside.

7. The measurement device according to claim 3,
wherein the first biological data is pulse data, and
the second measurement value is electrocardiogram data.

8. The measurement device according to claim 1,
wherein said first measurement unit is configured to measure the first biological data temporally consecutive k times to obtain the k first measurement values.

9. A measurement device comprising:
a first measurement unit configured to measure first biological data at least k times, where k≥2, to obtain any k first measurement values;
a distributed-signature generation unit configured to execute signature operations for the k first measurement values using any various k distributed-signature keys, respectively, to generate k distributed signatures, the k distributed-signature keys being capable of reconstructing a signature generation key only when all of the k distributed-signature keys are available;
a signature synthesis unit configured to synthesize the k distributed signatures together to reconstruct a signature;
a steady state verification unit configured to verify, using a signature verification key corresponding to the signature generation key, whether or not the signature reconstructed by said signature synthesis unit is correct, where the correctness of the signature means that the k first measurement values are same values; and
a quantization unit configured to quantize the k first measurement values obtained by said first measurement unit,
wherein said distributed-signature generation unit is configured to generate the k distributed signatures by executing the signature operations for the k first measurement values using the k distributed-signature keys, respectively, the k first measurement values being quantized by said quantization unit.

10. A method of controlling a measurement device, said method comprising:
measuring first biological data at least k times, where k≥2, to obtain any k first measurement values;
executing signature operations for the k first measurement values using any various k distributed-signature keys, respectively, to generate k distributed signatures, the k distributed-signature keys being capable of reconstructing a signature generation key only when all of the k distributed-signature keys are available;
synthesizing the k distributed signatures together to reconstruct a signature; and
verifying, using a signature verification key corresponding to the signature generation key, whether or not the signature reconstructed is correct where the correctness of the signature means that the k first measurement values are same values, wherein a result of a multiplication of the signature generation key and the signature verification key is a predetermined value, each of the signature operations is exponentiation where a corresponding one of the k distributed-signature keys or the signature generation key is an exponent, the signature generation key is generated by summing values of respective multiplications of the k distributed-signature keys by respective predetermined coefficients, in said executing, the k distributed signatures are generated by executing the exponentiation for the k first measurement values, respectively, a base of the exponentiation being each of the k first measurement values, and an exponent of the exponentiation being a distributed-signature key corresponding to the each of the k first measurement values among the k distributed-signature keys, in said synthesizing, the signature is calculated by raising the k distributed signatures respectively to power of the respective predetermined coefficients to generate k exponentiation results, and multiplying the k exponentiation results together, and in said verifying, a determination is made that the signature reconstructed in said synthesizing is correct, when a predetermined verification equation is satisfied, a left-hand side of the predetermined verification equation being exponentiation where the signature is a base and the signature verification key is an exponent, and a right-hand side of the predetermined verification equation being a target first measurement value from among the k first measurement values.

11. A computer program recorded on a non-transitory computer-readable recording medium for use in a computer, the computer program causing the computer to execute:

measuring first biological data at least k times, where k≥2, to obtain any k first measurement values;

executing signature operations for the k first measurement values using any various k distributed-signature keys, respectively, to generate k distributed signatures, the k distributed-signature keys being capable of reconstructing a signature generation key only when all of the k distributed-signature keys are available;

synthesizing the k distributed signatures together to reconstruct a signature; and verifying, using a signature verification key corresponding to the signature generation key, whether or not the signature reconstructed is correct, where the correctness of the signature means that the k first measurement values are same values, wherein a result of a multiplication of the signature generation key and the signature verification key is a predetermined value, each of the signature operations is exponentiation where a corresponding one of the k distributed-signature keys or the signature generation key is an exponent, the signature generation key is generated by summing values of respective multiplications of the k distributed-signature keys by respective predetermined coefficients, in said executing, the k distributed signatures are generated by executing the exponentiation for the k first measurement values, respectively, a base of the exponentiation being each of the k first measurement values, and an exponent of the exponentiation being a distributed-signature key corresponding to the each of the k first measurement values among the k distributed-signature keys, in said synthesizing, the signature is calculated by raising the k distributed signatures respectively to power of the respective predetermined coefficients to generate k exponentiation results, and multiplying the k exponentiation results together, and in said verifying, a determination is made that the signature reconstructed in said synthesizing is correct, when a predetermined verification equation is satisfied, a left-hand side of the predetermined verification equation being exponentiation where the signature is a base and the signature verification key is an exponent, and a right-hand side of the predetermined verification equation being a target first measurement value from among the k first measurement values.

12. An integrated circuit comprising:

a first measurement unit configured to measure first biological data at least k times, where k≥2, to calculate any k first measurement values;

a distributed-signature generation unit configured to execute signature operations for the k first measurement values using any various k distributed-signature keys, respectively, to generate k distributed signatures, the k distributed-signature keys being capable of reconstructing a signature generation key only when all of the k distributed-signature keys are available;

a signature synthesis unit configured to synthesize the k distributed signatures together to reconstruct a signature; and a steady state verification unit configured to verify, using a signature verification key corresponding to the signature generation key, whether or not the signature reconstructed by said signature synthesis unit is correct, where the correctness of the signature means that the k first measurement values are same values, wherein a result of a multiplication of the signature generation key and the signature verification key is a predetermined value, each of the signature operations is exponentiation where a corresponding one of the k distributed-signature keys or the signature generation key is an exponent, the signature generation key is generated by summing values of respective multiplications of the k distributed-signature keys by respective predetermined coefficients, said distributed-signature generation unit is configured to generate the k distributed signatures by executing the exponentiation for the k first measurement values, respectively, a base of the exponentiation being each of the k first measurement values, and an exponent of the exponentiation being a distributed-signature key corresponding to the each of the k first measurement values among the k distributed-signature keys, said signature synthesis unit is configured to calculate the signature by raising the k distributed signatures respectively to power of the respective predetermined coefficients to generate k exponentiation results, and multiplying the k exponentiation results together, and said steady state verification unit is configured to determine by the verification that the signature reconstructed by said signature synthesis unit is correct, when a predetermined verification equation is satisfied, a left-hand side of the predetermined verification equation being exponentiation where the signature is a base and the signature verification key is an exponent, and a right-hand side of the predetermined verification equation being a target first measurement value from among the k first measurement values.

* * * * *